(12) United States Patent
Stormo et al.

(10) Patent No.: US 8,301,388 B2
(45) Date of Patent: Oct. 30, 2012

(54) POOL AND SUPERPOOL MATRIX CODING AND DECODING DESIGNS AND METHODS

(75) Inventors: Keith E. Stormo, Moscow, ID (US);
QuanZhou Tao, Pullman, WA (US);
Robert Bogden, Moscow, ID (US)

(73) Assignee: Amplicon Express, Inc., Pullman, WA (US)

( * ) Notice: Subject to any disclaimer, the term of this patent is extended or adjusted under 35 U.S.C. 154(b) by 265 days.

(21) Appl. No.: 10/841,375

(22) Filed: May 5, 2004

(65) Prior Publication Data

US 2004/0224346 A1  Nov. 11, 2004

Related U.S. Application Data

(60) Provisional application No. 60/467,927, filed on May 5, 2003.

(51) Int. Cl.
*G01N 33/50* (2006.01)
(52) U.S. Cl. ......................................................... 702/19
(58) Field of Classification Search ........................ None
See application file for complete search history.

(56) References Cited

U.S. PATENT DOCUMENTS

| | | | | |
|---|---|---|---|---|
| 5,780,222 | A * | 7/1998 | Peddada et al. | 435/5 |
| 6,087,103 | A * | 7/2000 | Burmer | 506/4 |
| 6,187,544 | B1 * | 2/2001 | Bergsma et al. | 435/6 |
| 6,351,712 | B1 * | 2/2002 | Stoughton et al. | 702/19 |

OTHER PUBLICATIONS

Asakawa et al., Gene 191:69-79 (1997).*
BAC Library Pooling and Superpooling Users Manual, from Amplicon Express, available as indicated by Mar. 2003.*
Klein et al., A High-throughput AFLP-based Method for Constructing Integrated Genetic and Physical Maps: Progress Toward a Sorghum Genome Map, 2000, vol. 10, pp. 789-807.*

* cited by examiner

*Primary Examiner* — Jason Sims

(57) ABSTRACT

This application pertains to construction of pooled biological material such as DNA, RNA, proteins and the like that are able to be screened by a wide variety of methods such as PCR (Polymerase Chain Reaction), DNA/DNA hybridization, DNA/RNA hybridization, RNA/RNA hybridization, single strand DNA probing, protein/protein hybridization and a wide variety of additional methods. Our new method for construction of pools and superpools for screening differs in that the complete set is systematically divided into a variety of smaller subsets which are then re-pooled to make the final screening pools. This pooled material can be from individual samples or a population of samples. In order to reduce the analysis time, materials and expense, the pooling of high resolution small pools in a matrix allows for a lower number of user experiments to have higher resolution (as if the researcher had analyzed the complete set of small pools).

4 Claims, 5 Drawing Sheets

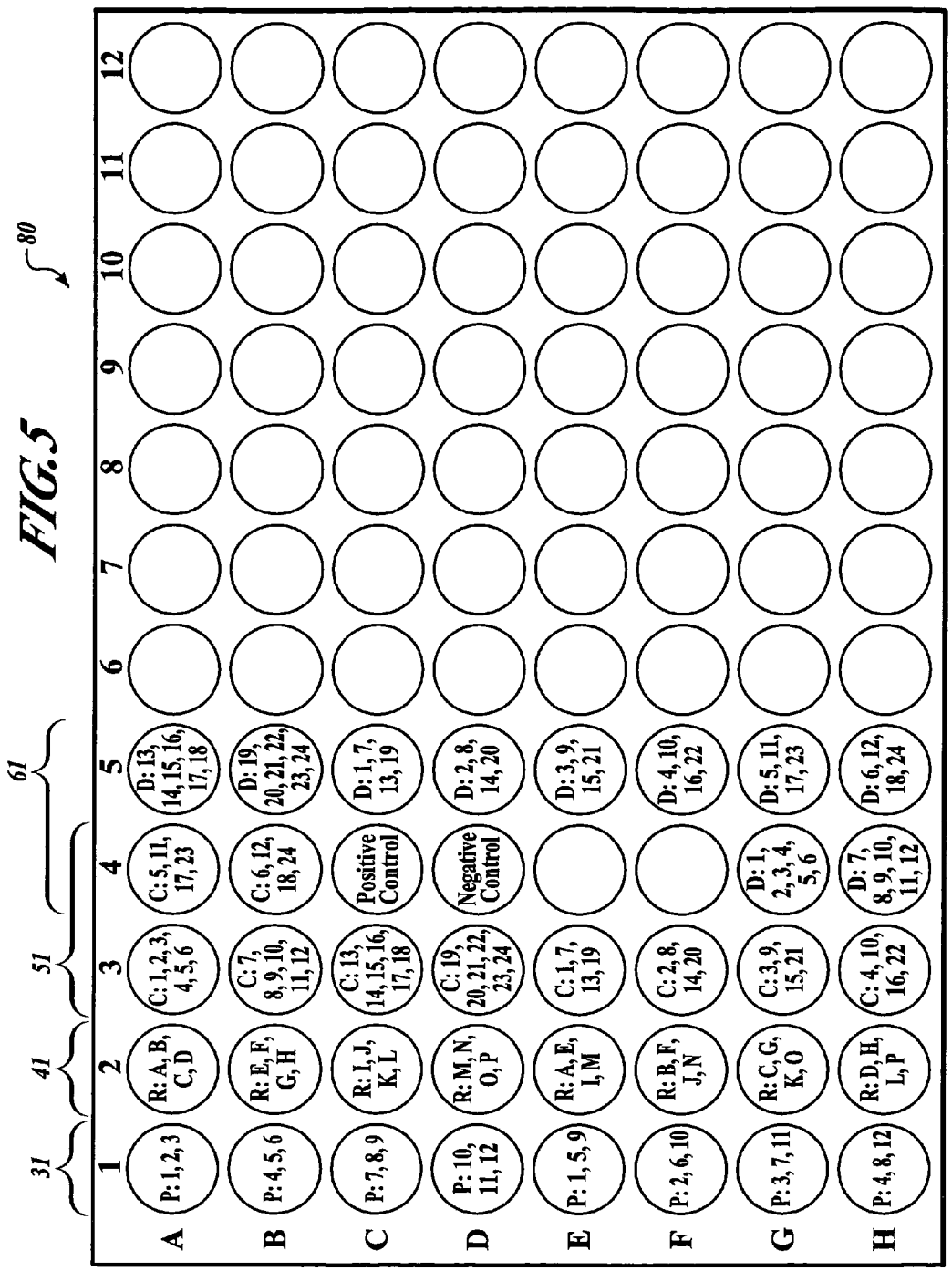

POOL AND SUPERPOOL MATRIX CODING AND DECODING DESIGNS AND METHODS

CROSS REFERENCE TO RELATED APPLICATIONS

This application claims the benefit of U.S. Provisional Patent Application Ser. No. 60/467,912, filed May 5, 2003 and entitled "Pool and Superpool matrix provisional application" now abandoned, which is herein incorporated by reference in its entirety for all purposes.

STATEMENT REGARDING FEDERALLY SPONSERED RESEARCH OR DEVELOPMENT

Not Applicable

REFERENCE TO SEQUENCE LISTING, A TABLE, OR A COMPUTER PROGRAM LISTING COMPACT DISK APPENDIX

Not Applicable
Field of Search: 341/., 435/., 435/ . . . , 435/DIG21, 435/DIG51, 536/23.1, 700/., 707/101
References Cited [Referenced By]
U.S. Patent Documents
  5,780,222
  6,126074
  6,477,699
  6,582,923
  6,607,888
  6,665,829
  6,706,867
  6,727,068
  6,727,071
Other References
  Ausubel et al., "Short Protocols in Molecular Biology", Wiley and Sons, New York.
  Sambrook et al., "Molecular Cloning, A Laboratory Manual", Cold Springs Harbor Press, New York.
  Torney et al., "Pooling of a Total Genomic BAC Library", US DOE Contract W-7405-ENG-36.
  Borm, T. J. A., BACBank on the Internet http://137.224.204.155/bacbank (also copied in provisional application 60/467,912).

BACKGROUND OF THE INVENTION

This application pertains to construction of pooled biological material such as DNA, RNA, proteins and the like that are able to be screened by a wide variety of methods such as PCR (Polymerase Chain Reaction), DNA/DNA hybridization, DNA/RNA hybridization, RNA/RNA hybridization, single strand DNA probing, protein/protein hybridization and a wide variety of additional methods. References describing many of these methods include "Ausubel et.al. Short Protocols in Molecular Biology, Wiley and Sons, New York" and "Sambrook et.al, Molecular Cloning, A Laboratory Manual, Cold Spring Harbor Press, New York" as well as numerous others and are hereby included by reference. Also included by reference are U.S. Pat. No. 5,780,222 (Method of PCR Testing of Pooled Blood Samples) and its references cited. Also included are U.S. Pat. Nos. 6,126,074 and 6,477,669 and their references including the references pertaining to Veterbi, Reed-Solomon and other Error Correction and Data Compression Coding schemes. This pooling method will allow the incorporation of 'loss-less information compression and error correction' or other 'current art' error correction strategies to improve the robustness of identification with significantly reduced numbers of samples to be processed by the end user. By having the samples pooled again after collection, it is possible to drastically reduce the manipulations required by the end user while still keeping very fine detail in the identification of the individual samples or populations that were originally pooled. These error-correction methods are well known in the computer data transmission field, but have not been used in the pooling of biological or chemical samples. The use of these methods will allow a large reduction in the number of experiments required to identify the specific biological sample or population containing a region of interest.

This pooled material can be from individuals or a population. In order to reduce the analysis time, materials and expense, the pooling of small high resolution pools in a matrix allows for a lower number of samples to be analyzed. The resulting high resolution data obtained from screening these matrix pools are equivalent to the data obtained if the researcher had analyzed the complete set of small pools (much more expensive, time consuming and difficult). This method also gives the added advantage of having two positive signals needed for identification. This reduces the problems associated with a false positive when only one signal is obtained for identification (as in the Current Art).

This matrix pooling can be just in one superpool. Alternatively, it can be a matrix of a variety of different superpools and/or across a variety of different types of pools to allow the screening of the complete library with just one round of experiments. To do this, each small pool would be added to between 6 and 20 of the collection of re-pooled intermediate or final pools. Then with the total number of pools of between 40 and 100, the complete library (or any set of biological samples) could be screened with high confidence and the ability to resolve multiple hits. If the library had a large redundancy of signal, the total number of pools could be increased to maintain accurate resolving power of the matrix method. The incorporation of positive controls in a matrix pattern can be used for quality assurance and for assisting in deconvolution if desired.

The current state of the art in pooling of biological materials such as Bacterial Artificial Chromosome (BAC) genomic DNA libraries (and other biological or chemical libraries like cDNA libraries, protein libraries, RNA libraries, DNA libraries cellular metabolic libraries and chemical libraries) for screening consist of the collection of all of the indexed microtiter plates containing the BAC library and then forming these plates into a large cube. These indexed plates are generally 96, 384, 864 well or sometimes even 1536 well microtiter plates. This large cube is then transected by a number of different planes (usually 4 to 8) which produce a large number of pools from each plane. This collection of all of the pools from all of the planes are then screened to identify the clones of interest. This scheme is the current state-of-the-art and can identify multiple clone hits with some degree of reliability to identify multiple targets (i.e. BAC clones) at a specific coordinate. According to Klein et al., their scheme with 6 planes in a collection of 24,576 BAC's could detect between 2 and 6 BAC's and over 90% could be reliably assigned to a specific coordinate with 184 screening pools (that is 184 user experiments are required).

Prior art as disclosed in S. Asakawa et al. Human BAC Library: Construction and Rapid Screening, Gene Vol. 191, pp. 69-79 (1979), may disclose some of the initial steps that are similar to the present invention in the Methods I section on page 72 but requires pooling clones before growth and requires construction of each screening pool directly from the pooled clones after growth.

The reason for the present invention accuracy, efficiency and reduced cost is that the present invention requires at least one additional step of repooling the intermediate subpooled genomic DNA clone DNA into a final screening pool, where the individual genomic DNA clone is in between three to ten unique final screening pools or between at least 4 unique Matrix Pools and no more than 8 unique Matrix Pools.

If the BAC Library is from an organism with a genome larger than 1,000 Mb, the researcher may find that there are very few ambiguous hits in the plate, row, column and diagonal (PRCD) plate. The Plate, Row, and Column pools correctly identify the clone of interest without the need for the Diagonal Pools. If the Diagonal Pools are only screened to solve the infrequent ambiguity, there would be a reduction in the number of PCR experiments.

A Bac-Bank is a way of storing fragments of DNA, together constituting the whole genome of an organism. The DNA of an organism is (semi) randomly cut in pieces, and these fragments are inserted into bacteria, which are then plated out so that a single colony grows from a single modified bacterium. Only modified bacteria are allowed to grow by using a bacterium that is potentially resistant to a certain antibiotic, and whose resistance is "switched on" by the presence of a foreign DNA fragment (insert), and by using a growth medium containing the antibiotic. The resulting (potentially) unique colonies of bacteria are then picked up individually and transferred to the wells of 384-well plates, and the resulting stack of plates holding a large number of unique bacteria, ideally containing the whole genome of the original organism, is known as a "Bac-Bank". It serves as a research database of the genome of the original organism. This database can be searched for fragments of DNA using PCR techniques.

Pooling is a method that allows one to quickly and economically search a Bac-Bank for the presence of certain DNA fragments. A Bac-Bank normally contains a large number of clones (~100,000), and testing all these clones individually for the presence of a fragment of DNA occurring only a few times (typically less than 100 times) in the original organism's genome is prohibitively expensive and laborious. When pooling is used the DNA of several clones is gathered into a much lower number of wells (pools), every well containing DNA from several clones and every clone's DNA being present in multiple wells. The distribution pattern ("pooling method", "pooling strategy","rule-set") is designed in such way that when using PCR reactions to screen the pools a pattern (of PCR reaction results) emerges that is (hopefully) unique to the clone(s) having the required properties. A simple example: take a 384-well plate having 16 rows of 24 columns; imagine pooling all wells horizontally and vertically, resulting in 16 row-pools and 24 column pools. If a single clone in this plate has a certain property, only the column-pool and the row-pool that particular clone is in will display a positive reaction when screened; the other 38 pools will be negative. Using only 40 PCR reaction it is therefore possible to pinpoint the positive clone in this 384-well plate; almost a tenfold reduction in labour and cost. As long as there are relatively few individuals with a certain property there is no problem; for properties that are shared among many individuals all pooling methods break down (yield incorrect results, either false-positives or (worse) false-negatives), and when this happens one has to resort to screening the clones individually.

Most often the individual clones in Bac-Bank are identified/labeled according to some hierarchical structure dictated by the physical properties of the Bac-Bank. The number of dimensions of a Bac-Bank is then related to the hierarchical structure of the storage format.

An example: The clones of a Bac-Bank are individually stored in wells on a plate. The wells are arranged in a rectangular pattern of rows and columns. If this plate constitutes the whole Bac-Bank this Bac-Bank can be viewed as one-dimensional if all the wells on the plate have consecutive numbers from left to right and top to bottom. One single parameter (well number) suffices to address every individual clone/well on the plate, and therefore the Bac-Bank is one-dimensional. A more natural approach in this example would be to address each well by its column and row numbers; then we would need two parameters to address an individual well, and therefore the same Bac-Bank can be two-dimensional as well.

For a larger Bac-Bank one plate would not suffice, and we could give each plate a separate ID code. This would add one coordinate to the number of coordinates required to address each individual well, and therefore there is one more dimension this case than there would before a single plate. Another approach is to store the well-plates in boxes of (for example) 10; each plate itself would then have two parameters (coordinates) for an address: the box number and (within that box) the plate number.

All these items are a matter or choice, and therefore the number of dimensions of a Bac-Bank is a choice as well; it is even possible to use several different addressing schemes without imposing any structure upon this number/code, but one may also choose to address an individual well as "[C, 23, 4, A, 6]", when the clone is located in fridge C, box 23, plate 4, column A, and row 6.

Having said this, it is important to note that it is most convenient to have some sort of logical structure related to the physical location of a clone; this helps you find individual clones faster, and most often there is also a relation between this logical/physical organization and the way the Bac-Bank is pooled. In all other examples we will assume that the Bac-Bank consists of 300 plates of 24×16 wells, and that the Bac-Bank is three-dimensional.

It will be readily apparent that there are a number of important claims that will arise from this disclosure, including but not limited to:

1. Higher resolution deconvolution of complex data without as many analysis reactions.
2. Analyzing a two, three or more-dimensional matrix of pools allows significant reduction in analysis reactions while retaining a high degree of specificity.
3. The incorporation of loss-less compression and error-correction into the pooling strategy allows improved robustness of analysis and identification if individuals from the pools with increased effectiveness while reducing the numbers of analysis.
4. Significantly reducing the number of analysis reactions required from other, less sophisticated pooling systems if a matrix re-pooling design is utilized.
5. As the analytical methods improve, the ability of re-pooling pools (that currently are at the limits of detection) is another significant improvement and advantage.

BRIEF SUMMARY OF THE INVENTION

Our new method differs in that the complete set is systematically divided into smaller subsets which are then re-pooled to make the final screening pools. This pooled material can be from individual samples or a population of samples. In order to reduce the analysis time, materials and expense, the pooling of high resolution small pools in a matrix allows for a lower number of user experiments to have higher resolution (as if the researcher had analyzed the complete set of small pools). One of the preferred embodiments describes a two step method that first screens for which superpool. Then that specific superpool's pools have been re-pooled into matrix pools (which are 36 matrix pools instead of 76 pools). The matrix pools are screened in this method also gives the added advantage of having two or more positive signals needed for identification (as shown in our provisional application). This reduces the current state-of-the-art problems associated with a false positive and/or false negative experimental result when only one signal is obtained for identification.

The Round I PCR is performed on all of the subpools "containing all BAC clones in the Library". Each Superpool contains 4,608 individual BAC clones. The results from Round I of PCR will identify which Superpool BAC clone(s) with the sequence of interest (there may be more than one Superpool identified). The researcher may chose to pursue one or more positive hits from the Round I PCR.

The Round II PCR will be performed on the Matrix Pools for the specific Superpool identified in Round I PCR. Round II PCR requires 36 PCR experiments plus controls (for each positive hit pursued from Round I PCR). The results from Round II PCR should allow the researcher to identify the plate and well position for several positive hits and to rule out many potential false positives (in the particular Superpool(s) being pursued). In comparison, using a traditional plate/row/column/diagonal strategy, Round II PCR screening of PRCD pools requires 76 PCR reactions plus controls. The Matrix system reduces the PCR experiments by 50%.

The Matrix Pools are PRCD pools combined so that EACH of these PRCD pools is contained in TWO unique Matrix Pools. There are a total of 36 Matrix Pools for each Superpool. Eight Matrix Plate Pools (MPP), eight Matrix Row Pools (MRP), 10 Matrix Column Pools (MCP) and 10 Matrix Diagonal Pools (MDP). There are at most 1,152 individual BAC clones inside each Matrix Pool well.

The matrix pooling can be just in one superpool (as we have shown in the detailed description of our matrix manual in our provisional application). Alternately, it can be a matrix of a variety of different superpools and/or across a variety of different types of pools to allow the screening of the complete library with just one round of experiments. To do this, each small pool would be combined with any number (generally between six and many thousands depending on the sensitivity/robustness of the users experimental screening strategy) of final collection pools (which are re-pooled intermediate pools). For this example we'll use the range of 6 and 20 collection pools (fully compatible with a PCR based screening technology). Then with the total number of pools of between 40 and 180, and more preferably between 80 and 96, the complete library could be screened with high confidence and the ability to resolve multiple samples in the library containing an identical region of interest. If the library had a large redundancy of signal, the total number of pools could be increased to maintain accurate resolving power of the matrix methodology. The incorporation of positive controls in a matrix pattern can be used to for quality assurance and for assisting in deconvolution if desired.

BRIEF DESCRIPTION OF THE SEVERAL VIEWS OF THE DRAWINGS

FIG. 5 is the further re-pooling a subset of the wells of FIG. 4 onto the Matrix Pool Plate or specific repooling designs in a Plate, Row, Column, and Diagonal matrix loading pattern.

DETAILED DESCRIPTION OF THE INVENTION

Figure 1:
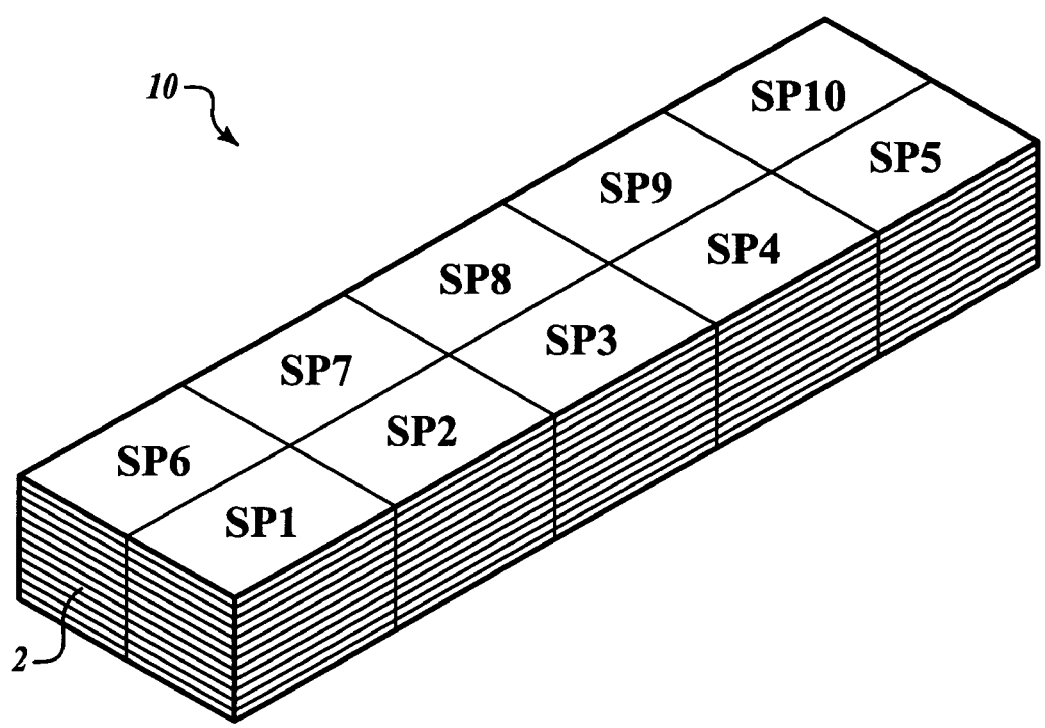
FIG. 1 is an entire BAC Library comprised of BAC clones in individual wells of 120, 384-well plates, designated as Superpools 1-10 (SP1-10).

FIGS. 1-5 are a graphical representation of an embodiment of the present invention. Example 2, Tables 6 and 7 are alternate embodiments of FIG. 3D and FIG. 4 respectively. Tables 8-11 represent additional alternative embodiments of specific repooling designs as depicted in FIG. 5. And Tables 12-16 are data from additional embodiments of the design techniques. FIG. 1 represents 10 Superpools of the entire 10 BAC Library containing 120, 384 well-plates 2 stacked on top of each other in 10 sets of 12 plates. A wide, almost limitless set of indexed microtiter plates may be used for the plates 2.

After compiling the Entire BAC Library the researcher receives two identical Superpool Collection Plates that are then used for Round I PCR.

Specifically, FIG. 1 is a combined stack of 10 Superpools (SP1-SP10). Each Superpool has a stack of 12 plates 2 stacked upon each other. The plates could be any multi-well unit that can be arranged into a hierarchical structure. Claimed herein are 96, 384, 864 and 1536-well units.

Figure 2:
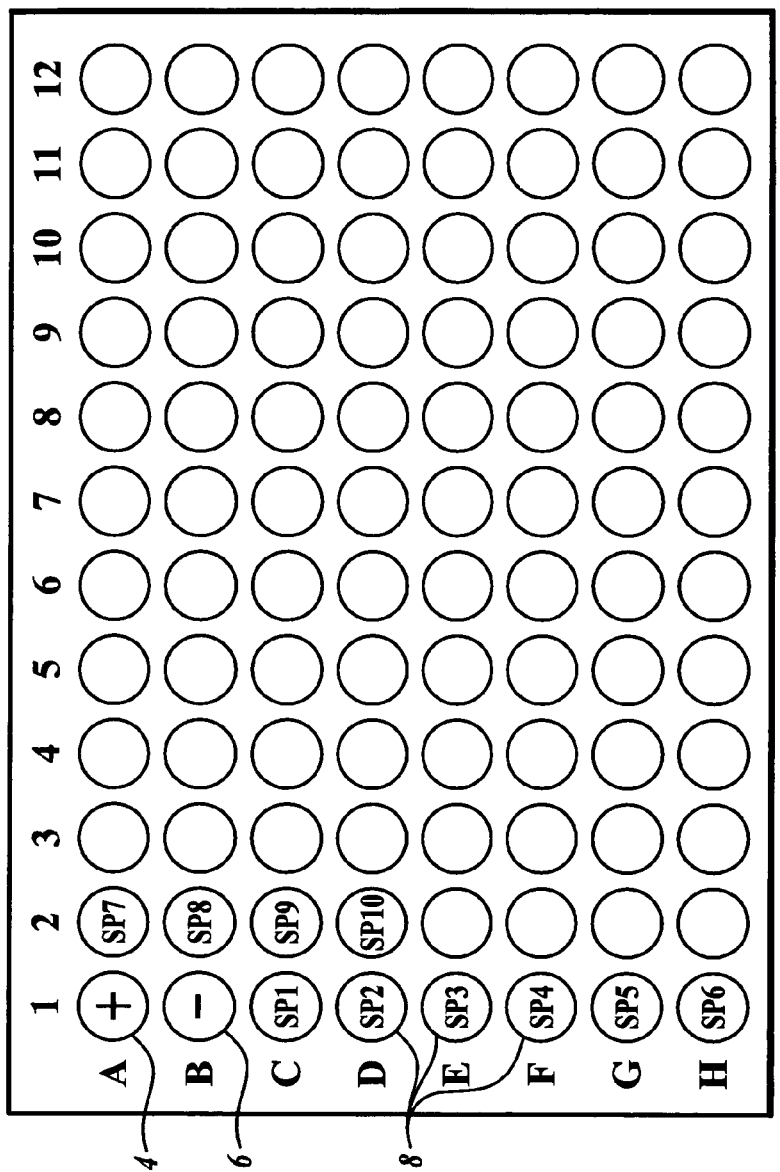
FIG. 2 is the Library Code Superpool Collection plate copy #1 having 96 wells.
Figure 3A:
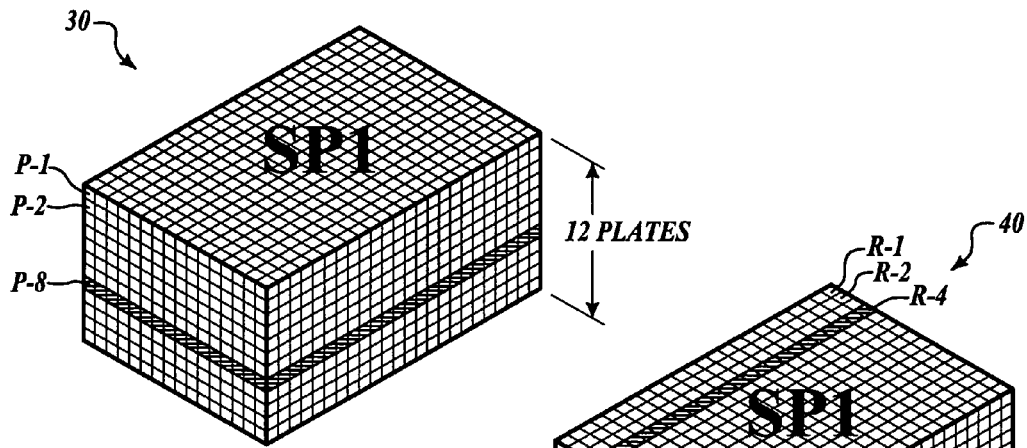
FIG. 3A is the SP1 with 12 plates having a clone address in plate #8.
Figure 3B:
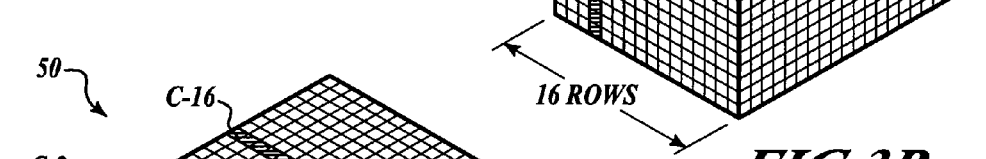
FIG. 3B is the SP1 with 16 rows having a clone address in row #4.
Figure 3C:
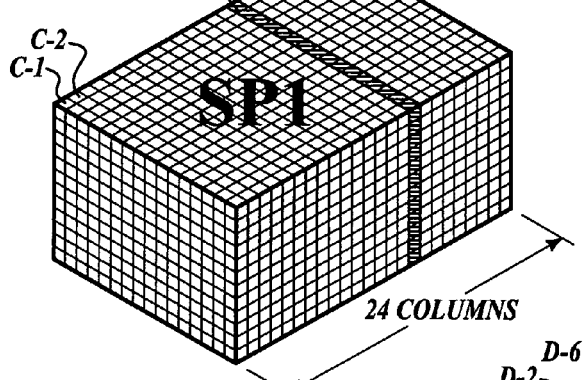
FIG. 3C is the SP1 with 24 columns having a clone address in column #16.
Figure 3D:
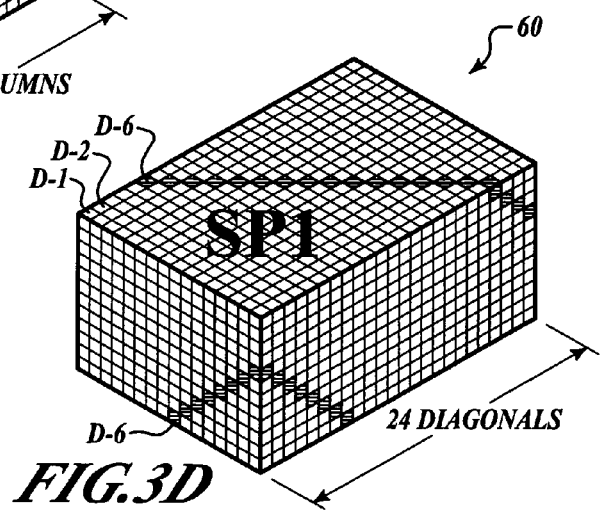
FIG. 3D is the SP1 with 24 diagonals having a clone address in diagonal #6 as specified in table 4.

In FIG. 2 a 96-well Superpool Plate 20 comes with a positive A1 and a negative control B1 4 and 6 respectively and a sample from each Superpool 8 and each Superpool plate provides the template for at least 800 PCR experiments.

After receiving Round I PCR gel electrophoresis results, the researcher determines which Superpool to screen for Round II PCR.

In FIG. 3 each Superpool SP-1 to SP-10 is then separated into pools of plates., rows, columns, and diagonals, which are all based on the hierarchical structure for the clone of interest to allow the researcher to find the specific coordinate or unique address of the well position with the clone of interest. At least three of these four hierarchical structures (plate, row, column, and diagonals) must be used or any combination of three of the four hierarchical structures, to insure or guarantee finding the specific coordinate well position with the clone of interest through iteration or redundancy (eg. FIG. 3D diagonal pool, plus FIG. 3A plate pool, plus FIG. 3C column pool). Again FIGS. 3A-3D represents the primary embodiment of a Superpool with a stack of 12 plates with 384 wells. The essence of FIG. 3 (A-D) is to use four different search patterns to find the precise well having the clone of interest. FIG.3A identifies the plate of interest in Superpool 1, 30 eg.P-8. FIG. 3B identifies the row of interest in SP1, 40, eg. R-4. FIG. 3C identifies the column of interest in SP1, 50, eg. C-16. FIG. 3D identifies the diagonal of interest in SP1, 60, eg. D-6.

Figure 4:
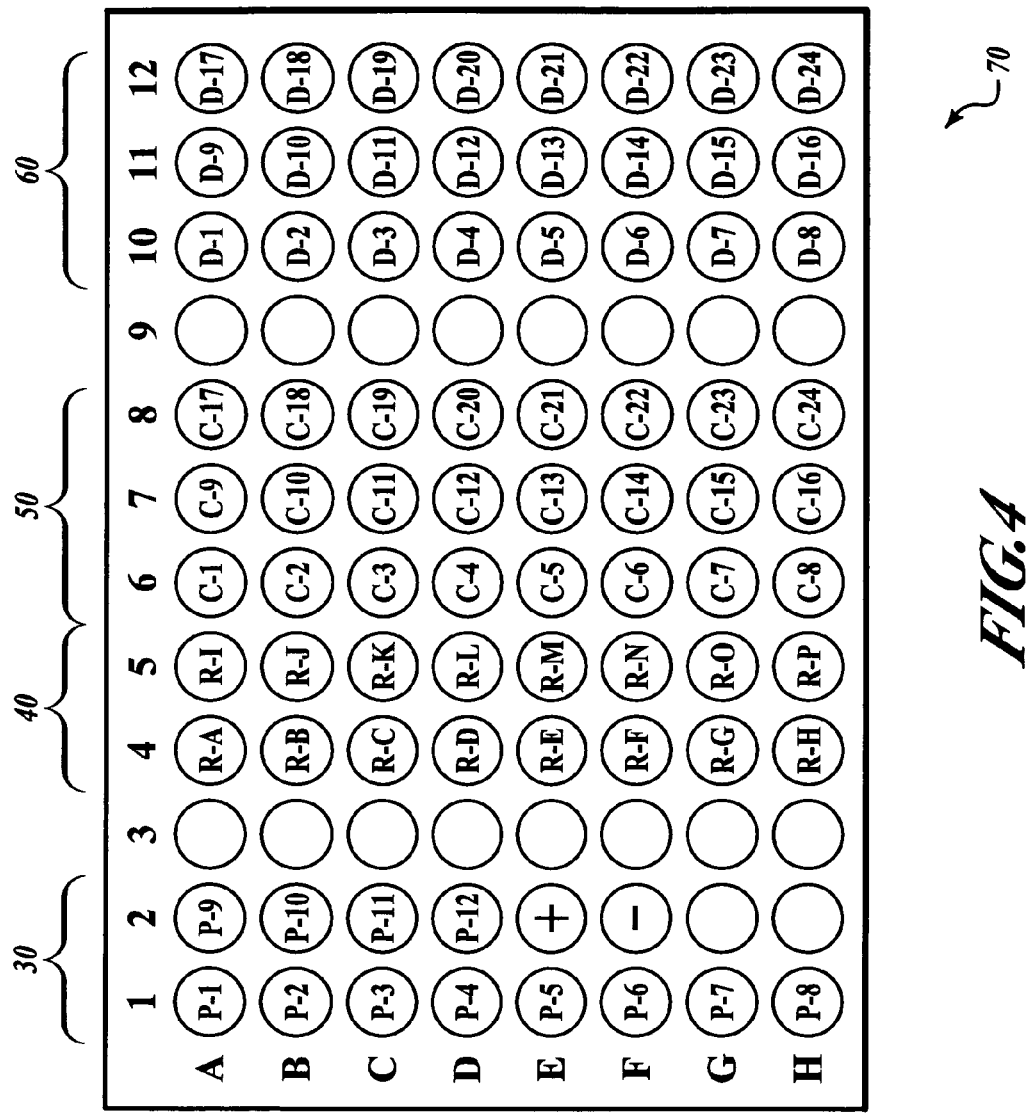
FIG. 4 is the small high resolution pools of the plate, row, column, and diagonal samples of DNA, cDNA or proteins with a positive and negative control in wells E2 and F2 respectively.

All of the DNA or protein samples in a Superpool from the plates 30, rows 40, columns 50, and diagonals 60 are sequentially pooled as represented in FIG. 4, onto a 96-well plate 70.

The plate 31, row 41, column 51, and diagonal 61 pooled DNA complete with positive and negative controls C4 and D4 respectively, are further re-pooling onto the Matrix Pool Plate FIG. 5, which for illustrative purposes is a 96-well plate 80. This combination further narrows the search for the well with the clone of interest. FIG. 4 depicts the complete set of intermediate subpools in the hierarchical structure plate pool 30, row pool 40, column pool 50 and diagonal pool 60 that were generated by processing each individual subpool to extract the necessary material according to the hierarchical structure. FIG. 4 is where the isolated material from the subpools is stored in a stable form before repooling each intermediate subpooled material into the Final Screening Pools as shown in FIG. 5.

Material from the complete set of intermediate subpools is further combined and repooled into the Matrix Pool Plate FIG. 5, the researcher will then receive two identical Matrix Pool Plates FIG. 5 for each Superpool to use to perform Round II PCR. FIG. 5 represents the key step to the present invention. FIG. 5 represents the repooling of the intermediate subpooled material into a number of final screening pools based on a specific repooling design, wherein individual information is in at least four final screening pools and no more than eight final screening pools. When the plate of final screening pool materials is screened, the specific coordinates are determined which allows the identification of the well position of the clone of interest.

EXAMPLE 1

Detailed Description of Pools & Superpools:

This description is based on 384 well index plates, but it could be used with other plate formats as well with appropriate considerations. It is also based on a BAC genomic DNA library comprised of individual BAC clones, but it could be used with a large variety of biological sample collections or chemical sample collections. The system consists of a collection of multiple Superpools that are screened during First Round PCR, to determine which set of Matrix Pools to screen during Second Round PCR. The total number of Superpools is determined by the total number of clones in the BAC library. Each Superpool has it's own 96-well plate of corresponding Matrix Pools.

Superpools: Each superpool consists of twelve consecutive 384-well plates from a BAC library. DNA is prepared by growing EACH BAC CLONE separately (to avoid growth competition between BAC clones) then combining the 4,608 cultures into one large-scale BAC prep. The Superpool of BAC DNA is then aliquoted onto a 96-well plate. Superpool SP-1 has all the BAC clones in the first twelve plates of the BAC library (Plate 001 to Plate 012).

Superpool SP-2 has all the BAC clones in the second twelve plates of the BAC library (Plate 013 to Plate 024). This naming continues for the entire library.

Matrix Pools: For each superpool there is one set Matrix Pools (this set of 36 Matrix Pools are aliquoted onto a Matrix Pool Plate. The Matrix Pools of Superpool #1 are named:
Matrix Plate Pools 1MPP-A1 through 1MPP-H1 for the 8 wells that contain the matrix of plates 1-12 in Superpool one. Each Matrix Plate Pool contains 1,152 clones. Table 1 indicates the clones in each well. The same process is repeated for as many superpools as are needed for the complete library.

TABLE 1

Matrix Plate Pools; Corresponding to FIG. 5, 31.

| Matrix well # | clones contained in plate # of the specific superpool |
|---|---|
| A1 | 1,2,3 |
| B1 | 4,5,6 |
| C1 | 7,8,9 |
| D1 | 10,11,12 |
| E1 | 1,5,9 |
| F1 | 2,6,10 |
| G1 | 3,7,11 |
| H1 | 4,8,12 |

Matrix Row Pools 1MRP-A2 through 1MRP-H2 for the 8 wells that contain the matrix of rows A-P in Superpool #1. Each Matrix Row Pool contains 1,152 clones for twelve 384 well plates. See table 2 for the composition of each well in the Matrix Row Pools.

TABLE 2

Matrix Row Pools; Corresponding to FIG. 5, 41.

| Matrix well # | Clones contained in row letter of the specific superpool |
|---|---|
| A2 | A,B,C,D |
| B2 | E,F,G,H |
| C2 | I,J,K,L |
| D2 | M,N,O,P |
| E2 | A,E,I,M |
| F2 | B,F,J,N |
| G2 | C,G,K,O |
| H2 | D,H,L,P |

Matrix Column Pools 1MPP-A3 through 1MPP-B4 for the 10 wells that contain the matrix of columns 1-24 in Superpool #1. See table 3 for the exact composition of each well in the Matrix Column Pools. The Matrix Column Pools in wells A3 through D3 have 1,152 clones (6 different columns X 192 column wells/plate=1,152 clones per Matrix Column Pool). The Matrix Column Pools in wells E3 through B4 contain 768 clones (4 different columns X 192 column wells/plate=768 clones per Matrix Row Pool).

TABLE 3

Matrix Column Pools; Corresponding to FIG. 5, 51.

| Matrix well # | Clones contained in column # of the specific Superpool |
|---|---|
| A3 | 1,2,3,4,5,6 |
| B3 | 7,8,9,10,11,12 |
| C3 | 13,14,15,16,17,18 |
| D3 | 19,20,21,22,23,24 |
| E3 | 1,7,13,19 |
| F3 | 2,8,14,20 |
| G3 | 3,9,15,21 |
| H3 | 4,10,16,22 |
| A4 | 5,11,17,23 |
| B4 | 6,12,18,24 |

Matrix Diagonal Pools 1MDP-G4 through 1MDP-H5 for the 10 wells that contain the matrix of diagonals 1-24 in Superpool #1. See table 4 for the exact composition of each pool in the Diagonal Pools. The diagonal pools are a collection of clones from all twelve plates in one superpool that has been transected by a plane that goes diagonal in an XY plane and diagonal in a XZ plane through the 12 plates. The diagonals are named by the number of the column that the clone from row A on plate 1 of the specific diagonal. Table 5 shows the exact composition of the Matrix Diagonal Pools. In wells G4 through B5 have 1,152 clones (6 different diagonals X 12 plates/diagonal X 16 column wells/plate=1,152 clones per Matrix Diagonal Pool). The Matrix Diagonal Pools in wells C5 through H5 contain 768 clones (4 different diagonals X 12 plates/diagonal X 16 column wells/plate=768 clones per Matrix Row Pool).

TABLE 4

Diagonal Pool Composition; Depicted graphically by FIG. 3D and correspondig to the construction of FIG. 4, 60.

| Diagonal pool # | clones contained in the specific superpool labeled by (plate, row, column) (note: as the column gets to 24, it wraps back to column 1 for a 16 row by 24 column plate) |
|---|---|
| 1 | 1A1,1B2,1C3 ... 1P16; 2A2,2B3,2C4 ... 2P17; ... ; 12A12,12B13,12C14 ... 12P3 |
| 2 | 1A2,1B3,1C4 ... 1P17; 2A3,2B4,2C5 ... 2P18; ... ; 12A13,12B14,12C15 ... 12P4 |
| 3 | 1A3,1B4,1C5 ... 1P18; 2A4,2B5,2C6 ... 2P19; ... ; 12A14,12B15,12C16 ... 12P5 |
| 4 | 1A4,1B5,1C6 ... 1P19; 2A5,2B6,2C7 ... 2P20; ... ; 12A15,12B16,12C17 ... 12P6 |
| 5 | 1A5,1B6,1C7 ... 1P20; 2A6,2B7,2C8 ... 2P21; ... ; 12A16,12B17,12C18 ... 12P7 |
| 6 | 1A6,1B7,1C8 ... 1P21; 2A7,2B8,2C9 ... 2P22; ... ; 12A17,12B18,12C19 ... 12P8 |
| 7 | 1A7,1B8,1C9 ... 1P22; 2A8,2B9,2C10 ... 2P23; ... ; 12A18,12B19,12C20 ... 12P9 |
| 8 | 1A8,1B9,1C10 ... 1P23; 2A9,2B10,2C11 ... 2P24; ... ; 12A19,12B20,12C21 ... 12P10 |
| 9 | 1A9,1B10,1C11 ... 1P24; 2A10,2B11,2C12 ... 2P1; ... ; 12A20,12B21,12C22 ... 12P11 |
| 10 | 1A10,1B11,1C12 ... 1P1; 2A11,2B12,2C13 ... 2P2; ... ; 12A21,12B22,12C23 ... 12P12 |
| 11 | 1A11,1B12,1C13 ... 1P2; 2A12,2B13,2C14 ... 2P3; ... ; 12A22,12B23,12C24 ... 12P13 |
| 12 | 1A12,1B13,1C14 ... 1P3; 2A13,2B14,2C15 ... 2P4; ... ; 12A23,12B24,12C1 ... 12P14 |
| 13 | 1A13,1B14,1C15 ... 1P4; 2A14,2B15,2C16 ... 2P5; ... ; 12A24,12B1,12C2 ... 12P15 |
| 14 | 1A14,1B15,1C16 ... 1P5; 2A15,2B16,2C17 ... 2P6; ... ; 12A1,12B2,12C3 ... 12P16 |
| 15 | 1A15,1B16,1C17 ... 1P6; 2A16,2B17,2C18 ... 2P7; ... ; 12A2,12B3,12C4 ... 12P17 |
| 16 | 1A16,1B17,1C18 ... 1P7; 2A17,2B18,2C19 ... 2P8; ... ; 12A3,12B4,12C5 ... 12P18 |
| 17 | 1A17,1B18,1C19 ... 1P8; 2A18,2B19,2C20 ... 2P9; ... ; 12A4,12B5,12C6 ... 12P19 |
| 18 | 1A18,1B19,1C20 ... 1P9; 2A19,2B20,2C21 ... 2P10; ... ; 12A5,12B6,12C7 ... 12P20 |
| 19 | 1A19,1B20,1C21 ... 1P10; 2A20,2B21,2C22 ... 2P11; ... ; 12A6,12B7,12C8 ... 12P21 |
| 20 | 1A20,1B21,1C22 ... 1P11; 2A21,2B22,2C23 ... 2P12; ... ; 12A7,12B8,12C9 ... 12P22 |
| 21 | 1A21,1B22,1C23 ... 1P12; 2A22,2B23,2C24 ... 2P13; ... ; 12A8,12B9,12C10 ... 12P23 |
| 22 | 1A22,1B23,1C24 ... 1P13; 2A23,2B24,2C1 ... 2P14; ... ; 12A9,12B10,12C11 ... 12P24 |
| 23 | 1A23,1B24,1C1 ... 1P14; 2A24,2B1,2C2 ... 2P15; ... ; 12A10,12B11,12C12 ... 12P1 |
| 24 | 1A24,1B1,1C2 ... 1P15; 2A1,2B2,2C3 ... 2P16; ... ; 12A11,12B12,12C13 ... 12P2 |

It is clear that this table is but just an example of a diagonal scheme that is non-redundant with other pools. This table is not limited to one specific diagonal, since there are additional diagonal strategies that can also included as obvious expansions on this diagonal strategy.

TABLE 5

Matrix Diagonal Pools; Corresponding to FIG. 5, 61.

| Matrix well # | Clones contained in diagonal # of the specific superpool |
|---|---|
| G4 | 1,2,3,4,5,6 |
| H4 | 7,8,9,10,11,12 |
| A5 | 13,14,15,16,17,18 |
| B5 | 19,20,21,22,23,24 |
| C5 | 1,7,13,19 |
| D5 | 2,8,14,20 |
| E5 | 3,9,15,21 |
| F5 | 4,10,16,22 |
| G5 | 5,11,17,23 |
| H5 | 6,12,18,24 |

After screening the matrix pools by one of many possible methods, the identity of a specific positive clone from the library can be determined. The specific identification can be determined by a number of ways. If the pool design and matrix design are written or available in electronic form, the unique clone can be identified by a visual or electronic search. There can also be algorithms written based on the pool and matrix designs that can identify the unique clone.

The second example describes a method to form a matrix of a variety of different superpools and/or across a variety of different types of pools to allow the screening of the complete library with just one round of experiments. To do this, each small pool or subpool would be added to between 6 and 20 of the collection of re-pooled intermediate or final pools. Then with the total number of pools of between 40 and 180, and more preferably between 80 and 94, the complete library could be screened with high confidence and the ability to resolve multiple hits. If the library had a large redundancy of signal, the total number of pools could be increased to maintain accurate resolving power of the matrix solution. Note: 94 experiments is the preferred number, because current screening technologies are performed on a 96-well index plate format (94 experiments will allow room for a positive control and negative control).

In the second example we will teach an additional method that allows the complete library to be screened in one step while still maintaining the resolution of the superpool individual pools formed in Example 1.

EXAMPLE 2

This example further illustrates and teaches the advantages and possibilities of the current invention. This example is also based on 384 well index plates, but it could be used with other plate formats as well with appropriate considerations. It is also based on a BAC genomic DNA library comprised of individual BAC clones, but it could be used with a large variety of biological collections. The superpools will be composed of eight 384 well plates per superpool and with 10 superpools combined into one large set of matrix pools. Therefore there will be 80 plates (30,720 individual BAC clones in the library) in this one matrix screening that can be tested with a limited number of tests while still maintaining good resolution to an individual clone or may possibly requires screening a few clones during the clone confirmation test directly on the clone(s) of interest. This scheme also allows a single set of experiments (instead of two sets of experiments as described in Example 1).

In this scheme, the individual superpools are numbered so that each individual ⅓ plate, row, column and diagonal pool has a unique number. Since there are 88 pools per superpool and ten superpools in this example, there are a total of 880 individual pools that will be combines into one large set of matrix pools. Depending on the number of redundant clones in the BAC library (a function of the genome size and the insert size of the BAC clones), the idealized degree of redundancy can dramatically improve the ability to identify multiple positive clones in one screening and thus minimize ambiguous results (when the user is analyzing data from the screening experiments).

The first ⅓ plate pools are formed by collecting all of the clones in plate 1 from columns 1-8. Then the second ⅓ plate pool is all of the clones from columns 9-16 of plate one. This continues on until the $24^{th}$ ⅓ plate pool is from columns 17-24 of plate 8. The twenty-four ⅓ plate pools from superpool two would be considered being in pools 89-112 and so on until the tenth superpool where the ⅓ plate pools would be in pools 793-816.

The row pools would be built the same way as Example 1 but since there are only 8 plates in each superpool, each pool would have 192 clones. All of the clones in row A of the eight plates would be pooled together and these clones would be considered pool number 25. This would continue on in a similar fashion so all of the clones in row B of all eight plates of the superpool would belong to pool 26 (and so on) until finally, the pool of all of the clones in row P of the first eight plates would belong to pool number 40. Similarly, the row pools from the second superpool will be in pools numbered 113-128. This would continue in a similar fashion until all of the superpool individual clones belong to row pools and each are assigned unique numbers.

The column pools would be formed the same way as in Example 1 but since there are only 8 plates in each superpool, each pool would have 128 clones. All of the clones in column 1 of the eight plates would be pooled together and would belong to pool number 41. This would continue on in a similar fashion until all of the clones in column 2 of all eight plates of the superpool would belong to pool 42 (and so on). Until finally, the pool of all of the clones in column 24 of the first eight plates belong to pool number 64. Similarly, the column pools from the second superpool will be in pools numbered 129-152. This would continue in a similar fashion until all of the superpools belong to column pools and each are assigned unique numbers.

The diagonal pools would be formed the same way as in Example 1 but since there are only 8 plates in each superpool, each pool would have 128 clones. See table 6 for the 8 plate superpool diagonal composition. All of the clones in diagonal 1 of the eight plates would be pooled together and would belong to pool number 65. This would continue on in a similar fashion until all of the clones in diagonal 2 of all eight plates of the superpool would belong to pool 66 (and so on). Until finally, the pool of all of the clones in diagonal 24 of the first eight plates belong to pool number 88. Similarly, the diagonal pools from the second superpool will be in pools numbered 152-176. This would continue in a similar fashion until all of the superpools belong to diagonal pools and each are assigned unique numbers.

To see one design of many possible schemes for identifying a complete set unique pool numbers, please see Table 7. Table 7 is designed for 88 pools in each subset (superpool) and ten subset (superpools) in the complete set. These unique pool numbers are used to construct various tested screening pool pooling strategies.

TABLE 6

Diagonal pool composition for a 8 plate superpool.

| Diagonal pool # | clones contained in the specific superpool labeled by (plate, row, column) (note: as the column gets to 24, it wraps back to column 1 for a 16 row by 24 column plate) |
|---|---|
| 1 | 1A1,1B2,1C3 . . . 1P16; 2A2,2B3,2C4 . . . 2P17; . . . ; 8A8,8B9,8C10 . . . 8P23 |
| 2 | 1A2,1B3,1C4 . . . 1P17; 2A3,2B4,2C5 . . . 2P18; . . . ; 8A9,8B10,8C11 . . . 8P24 |
| 3 | 1A3,1B4,1C5 . . . 1P18; 2A4,2B5,2C6 . . . 2P19; . . . ; 8A10,8B11,12C12 . . . 8P1 |
| 4 | 1A4,1B5,1C6 . . . 1P19; 2A5,2B6,2C7 . . . 2P20; . . . ; 8A11,8B12,8C13 . . . 8P2 |
| 5 | 1A5,1B6,1C7 . . . 1P20; 2A6,2B7,2C8 . . . 2P21; . . . ; 8A12,8B13,8C14 . . . 8P3 |
| 6 | 1A6,1B7,1C8 . . . 1P21; 2A7,2B8,2C9 . . . 2P22; . . . ; 8A13,8B14,8C15 . . . 8P4 |
| 7 | 1A7,1B8,1C9 . . . 1P22; 2A8,2B9,2C10 . . . 2P23; . . . ; 8A14,8B15,8C16 . . . 8P5 |
| 8 | 1A8,1B9,1C10 . . . 1P23; 2A9,2B10,2C11 . . . 2P24; . . . ; 8A15,8B16,8C17 . . . 8P6 |
| 9 | 1A9,1B10,1C11 . . . 1P24; 2A10,2B11,2C12 . . . 2P1; . . . ; 8A16,8B17,8C18 . . . 8P7 |
| 10 | 1A10,1B11,1C12 . . . 1P1; 2A11,2B12,2C13 . . . 2P2; . . . ; 8A17,8B18,8C19 . . . 8P8 |
| 11 | 1A11,1B12,1C13 . . . 1P2; 2A12,2B13,2C14 . . . 2P3; . . . ; 8A18,8B19,8C20 . . . 8P9 |
| 12 | 1A12,1B13,1C14 . . . 1P3; 2A13,2B14,2C15 . . . 2P4; . . . ; 8A19,8B20,8C21 . . . 8P10 |
| 13 | 1A13,1B14,1C15 . . . 1P4; 2A14,2B15,2C16 . . . 2P5; . . . ; 8A20,8B21,8C22 . . . 8P11 |
| 14 | 1A14,1B15,1C16 . . . 1P5; 2A15,2B16,2C17 . . . 2P6; . . . ; 8A21,8B22,8C23 . . . 8P12 |
| 15 | 1A15,1B16,1C17 . . . 1P6; 2A16,2B17,2C18 . . . 2P7; . . . ; 8A22,8B23,8C24 . . . 8P13 |
| 16 | 1A16,1B17,1C18 . . . 1P7; 2A17,2B18,2C19 . . . 2P8; . . . ; 8A23,8B24,8C1 . . . 8P14 |
| 17 | 1A17,1B18,1C19 . . . 1P8; 2A18,2B19,2C20 . . . 2P9; . . . ; 8A24,8B1,8C2 . . . 8P15 |
| 18 | 1A18,1B19,1C20 . . . 1P9; 2A19,2B20,2C21 . . . 2P10; . . . ; 8A1,8B2,8C3 . . . 8P16 |
| 19 | 1A19,1B20,1C21 . . . 1P10; 2A20,2B21,2C22 . . . 2P11; . . . ; 8A2,8B3,8C4 . . . 8P17 |
| 20 | 1A20,1B21,1C22 . . . 1P11; 2A21,2B22,2C23 . . . 2P12; . . . ; 8A3,8B4,8C5 . . . 8P18 |
| 21 | 1A21,1B22,1C23 . . . 1P12; 2A22,2B23,2C24 . . . 2P13; . . . ; 8A4,8B5,8C6 . . . 8P19 |
| 22 | 1A22,1B23,1C24 . . . 1P13; 2A23,2B24,2C1 . . . 2P14; . . . ; 8A5,8B6,8C7 . . . 8P20 |
| 23 | 1A23,1B24,1C1 . . . 1P14; 2A24,2B1,2C2 . . . 2P15; . . . ; 8A6,8B7,8C8 . . . 8P21 |
| 24 | 1A24,1B1,1C2 . . . 1P15; 2A1,2B2,2C3 . . . 2P16; . . . ; 8A7,8B8,8C9 . . . 8P22 |

Table 7 sequentially assigns numbers to individual small pools or subpools from ten consecutive from eight plates so that the subpools may be repooled into final screening pools according to example alternative embodiments depicted in tables 8-11.

TABLE 7

Unique pool numbers for the 1/3 plate, row, column and diagonal pools of the first ten superpools.

| Individual superpool contents | Unique pool numbers for 8 plate superpools 1 through 10. | | | | | | | | | |
|---|---|---|---|---|---|---|---|---|---|---|
| | 1 | 2 | 3 | 4 | 5 | 6 | 7 | 8 | 9 | 10 |
| 1/3 plate 1 | 1 | 89 | 177 | 265 | 353 | 441 | 529 | 617 | 705 | 793 |
| 1/3 plate 2 | 2 | 90 | 178 | 266 | 354 | 442 | 530 | 618 | 706 | 794 |
| 1/3 plate 3 | 3 | 91 | 179 | 267 | 355 | 443 | 531 | 619 | 707 | 795 |
| 1/3 plate 4 | 4 | 92 | 180 | 268 | 356 | 444 | 532 | 620 | 708 | 796 |
| 1/3 plate 5 | 5 | 93 | 181 | 269 | 357 | 445 | 533 | 621 | 709 | 797 |
| 1/3 plate 6 | 6 | 94 | 182 | 270 | 358 | 446 | 534 | 622 | 710 | 798 |
| 1/3 plate 7 | 7 | 95 | 183 | 271 | 359 | 447 | 535 | 623 | 711 | 799 |
| 1/3 plate 8 | 8 | 96 | 184 | 272 | 360 | 448 | 536 | 624 | 712 | 800 |
| 1/3 plate 9 | 9 | 97 | 185 | 273 | 361 | 449 | 537 | 625 | 713 | 801 |
| 1/3 plate 10 | 10 | 98 | 186 | 274 | 362 | 450 | 538 | 626 | 714 | 802 |
| 1/3 plate 11 | 11 | 99 | 187 | 275 | 363 | 451 | 539 | 627 | 715 | 803 |
| 1/3 plate 12 | 12 | 100 | 188 | 276 | 364 | 452 | 540 | 628 | 716 | 804 |
| 1/3 plate 13 | 13 | 101 | 189 | 277 | 365 | 453 | 541 | 629 | 717 | 805 |
| 1/3 plate 14 | 14 | 102 | 190 | 278 | 366 | 454 | 542 | 630 | 718 | 806 |
| 1/3 plate 15 | 15 | 103 | 191 | 279 | 367 | 455 | 543 | 631 | 719 | 807 |
| 1/3 plate 16 | 16 | 104 | 192 | 280 | 368 | 456 | 544 | 632 | 720 | 808 |
| 1/3 plate 17 | 17 | 105 | 193 | 281 | 369 | 457 | 545 | 633 | 721 | 809 |
| 1/3 plate 18 | 18 | 106 | 194 | 282 | 370 | 458 | 546 | 634 | 722 | 810 |
| 1/3 plate 19 | 19 | 107 | 195 | 283 | 371 | 459 | 547 | 635 | 723 | 811 |
| 1/3 plate 20 | 20 | 108 | 196 | 284 | 372 | 460 | 548 | 636 | 724 | 812 |
| 1/3 plate 21 | 21 | 109 | 197 | 285 | 373 | 461 | 549 | 637 | 725 | 813 |
| 1/3 plate 22 | 22 | 110 | 198 | 286 | 374 | 462 | 550 | 638 | 726 | 814 |
| 1/3 plate 23 | 23 | 111 | 199 | 287 | 375 | 463 | 551 | 639 | 727 | 815 |
| 1/3 plate 24 | 24 | 112 | 200 | 288 | 376 | 464 | 552 | 640 | 728 | 816 |
| row A | 25 | 113 | 201 | 289 | 377 | 465 | 553 | 641 | 729 | 817 |
| row B | 26 | 114 | 202 | 290 | 378 | 466 | 554 | 642 | 730 | 818 |
| row C | 27 | 115 | 203 | 291 | 379 | 467 | 555 | 643 | 731 | 819 |
| row D | 28 | 116 | 204 | 292 | 380 | 468 | 556 | 644 | 732 | 820 |
| row E | 29 | 117 | 205 | 293 | 381 | 469 | 557 | 645 | 733 | 821 |
| row F | 30 | 118 | 206 | 294 | 382 | 470 | 558 | 646 | 734 | 822 |
| row G | 31 | 119 | 207 | 295 | 383 | 471 | 559 | 647 | 735 | 823 |
| row H | 32 | 120 | 208 | 296 | 384 | 472 | 560 | 648 | 736 | 824 |
| row I | 33 | 121 | 209 | 297 | 385 | 473 | 561 | 649 | 737 | 825 |
| row J | 34 | 122 | 210 | 298 | 386 | 474 | 562 | 650 | 738 | 826 |
| row K | 35 | 123 | 211 | 299 | 387 | 475 | 563 | 651 | 739 | 827 |
| row L | 36 | 124 | 212 | 300 | 388 | 476 | 564 | 652 | 740 | 828 |
| row M | 37 | 125 | 213 | 301 | 389 | 477 | 565 | 653 | 741 | 829 |
| row N | 38 | 126 | 214 | 302 | 390 | 478 | 566 | 654 | 742 | 830 |
| row O | 39 | 127 | 215 | 303 | 391 | 479 | 567 | 655 | 743 | 831 |
| row P | 40 | 128 | 216 | 304 | 392 | 480 | 568 | 656 | 744 | 832 |
| column 1 | 41 | 129 | 217 | 305 | 393 | 481 | 569 | 657 | 745 | 833 |
| column 2 | 42 | 130 | 218 | 306 | 394 | 482 | 570 | 658 | 746 | 834 |
| column 3 | 43 | 131 | 219 | 307 | 395 | 483 | 571 | 659 | 747 | 835 |
| column 4 | 44 | 132 | 220 | 308 | 396 | 484 | 572 | 660 | 748 | 836 |
| column 5 | 45 | 133 | 221 | 309 | 397 | 485 | 573 | 661 | 749 | 837 |
| column 6 | 46 | 134 | 222 | 310 | 398 | 486 | 574 | 662 | 750 | 838 |
| column 7 | 47 | 135 | 223 | 311 | 399 | 487 | 575 | 663 | 751 | 839 |
| column 8 | 48 | 136 | 224 | 312 | 400 | 488 | 576 | 664 | 752 | 840 |
| column 9 | 49 | 137 | 225 | 313 | 401 | 489 | 577 | 665 | 753 | 841 |
| column 10 | 50 | 138 | 226 | 314 | 402 | 490 | 578 | 666 | 754 | 842 |
| column 11 | 51 | 139 | 227 | 315 | 403 | 491 | 579 | 667 | 755 | 843 |
| column 12 | 52 | 140 | 228 | 316 | 404 | 492 | 580 | 668 | 756 | 844 |
| column 13 | 53 | 141 | 229 | 317 | 405 | 493 | 581 | 669 | 757 | 845 |
| column 14 | 54 | 142 | 230 | 318 | 406 | 494 | 582 | 670 | 758 | 846 |
| column 15 | 55 | 143 | 231 | 319 | 407 | 495 | 583 | 671 | 759 | 847 |
| column 16 | 56 | 144 | 232 | 320 | 408 | 496 | 584 | 672 | 760 | 848 |
| column 17 | 57 | 145 | 233 | 321 | 409 | 497 | 585 | 673 | 761 | 849 |
| column 18 | 58 | 146 | 234 | 322 | 410 | 498 | 586 | 674 | 762 | 850 |
| column 19 | 59 | 147 | 235 | 323 | 411 | 499 | 587 | 675 | 763 | 851 |
| column 20 | 60 | 148 | 236 | 324 | 412 | 500 | 588 | 676 | 764 | 852 |
| column 21 | 61 | 149 | 237 | 325 | 413 | 501 | 589 | 677 | 765 | 853 |
| column 22 | 62 | 150 | 238 | 326 | 414 | 502 | 590 | 678 | 766 | 854 |
| column 23 | 63 | 151 | 239 | 327 | 415 | 503 | 591 | 679 | 767 | 855 |
| column 24 | 64 | 152 | 240 | 328 | 416 | 504 | 592 | 680 | 768 | 856 |
| diagonal 1 | 65 | 153 | 241 | 329 | 417 | 505 | 593 | 681 | 769 | 857 |
| diagonal 2 | 66 | 154 | 242 | 330 | 418 | 506 | 594 | 682 | 770 | 858 |
| diagonal 3 | 67 | 155 | 243 | 331 | 419 | 507 | 595 | 683 | 771 | 859 |
| diagonal 4 | 68 | 156 | 244 | 332 | 420 | 508 | 596 | 684 | 772 | 860 |
| diagonal 5 | 69 | 157 | 245 | 333 | 421 | 509 | 597 | 685 | 773 | 861 |
| diagonal 6 | 70 | 158 | 246 | 334 | 422 | 510 | 598 | 686 | 774 | 862 |
| diagonal 7 | 71 | 159 | 247 | 335 | 423 | 511 | 599 | 687 | 775 | 863 |
| diagonal 8 | 72 | 160 | 248 | 336 | 424 | 512 | 600 | 688 | 776 | 864 |

TABLE 7-continued

Unique pool numbers for the 1/3 plate, row, column and diagonal pools of the first ten superpools.

| Individual superpool contents | Unique pool numbers for 8 plate superpools 1 through 10. | | | | | | | | | |
|---|---|---|---|---|---|---|---|---|---|---|
| | 1 | 2 | 3 | 4 | 5 | 6 | 7 | 8 | 9 | 10 |
| diagonal 9 | 73 | 161 | 249 | 337 | 425 | 513 | 601 | 689 | 777 | 865 |
| diagonal 10 | 74 | 162 | 250 | 338 | 426 | 514 | 602 | 690 | 778 | 866 |
| diagonal 11 | 75 | 163 | 251 | 339 | 427 | 515 | 603 | 691 | 779 | 867 |
| diagonal 12 | 76 | 164 | 252 | 340 | 428 | 516 | 604 | 692 | 780 | 868 |
| diagonal 13 | 77 | 165 | 253 | 341 | 429 | 517 | 605 | 693 | 781 | 869 |
| diagonal 14 | 78 | 166 | 254 | 342 | 430 | 518 | 606 | 694 | 782 | 870 |
| diagonal 15 | 79 | 167 | 255 | 343 | 431 | 519 | 607 | 695 | 783 | 871 |
| diagonal 16 | 80 | 168 | 256 | 344 | 432 | 520 | 608 | 696 | 784 | 872 |
| diagonal 17 | 81 | 169 | 257 | 345 | 433 | 521 | 609 | 697 | 785 | 873 |
| diagonal 18 | 82 | 170 | 258 | 346 | 434 | 522 | 610 | 698 | 786 | 874 |
| diagonal 19 | 83 | 171 | 259 | 347 | 435 | 523 | 611 | 699 | 787 | 875 |
| diagonal 20 | 84 | 172 | 260 | 348 | 436 | 524 | 612 | 700 | 788 | 876 |
| diagonal 21 | 85 | 173 | 261 | 349 | 437 | 525 | 613 | 701 | 789 | 877 |
| diagonal 22 | 86 | 174 | 262 | 350 | 438 | 526 | 614 | 702 | 790 | 878 |
| diagonal 23 | 87 | 175 | 263 | 351 | 439 | 527 | 615 | 703 | 791 | 879 |
| diagonal 24 | 88 | 176 | 264 | 352 | 440 | 528 | 616 | 704 | 792 | 880 |

Tables 8-11 describe various embodiments in the systematic or randomization of the loading of the small pool or subpool plate, row, column, and diagonal pooled DNA (FIG. 4) into an alternate Matrix Pool Plate format (FIG. 5).

TABLE 8

Example 3 screening pool design.
94 seq 5 screening pool design

| Screening pool # | Unique pools contained in each screening pool | | | | | | | | | | |
|---|---|---|---|---|---|---|---|---|---|---|---|
| 1 | 1 | 95 | 189 | 283 | 377 | 471 | 565 | 659 | 753 | 847 | 301 | 827 |
| 2 | 2 | 96 | 190 | 284 | 378 | 472 | 566 | 660 | 754 | 848 | 302 | 828 |
| 3 | 3 | 97 | 191 | 285 | 379 | 473 | 567 | 661 | 755 | 849 | 303 | 829 |
| 4 | 4 | 98 | 192 | 286 | 380 | 474 | 568 | 662 | 756 | 850 | 304 | 830 |
| 5 | 5 | 99 | 193 | 287 | 381 | 475 | 569 | 663 | 757 | 851 | 377 | 831 |
| 6 | 6 | 100 | 194 | 288 | 382 | 476 | 570 | 664 | 758 | 852 | 378 | 832 |
| 7 | 7 | 101 | 195 | 289 | 383 | 477 | 571 | 665 | 759 | 853 | 379 | |
| 8 | 8 | 102 | 196 | 290 | 384 | 478 | 572 | 666 | 760 | 854 | 380 | |
| 9 | 9 | 103 | 197 | 291 | 385 | 479 | 573 | 667 | 761 | 855 | 381 | |
| 10 | 10 | 104 | 198 | 292 | 386 | 480 | 574 | 668 | 762 | 856 | 382 | |
| 11 | 11 | 105 | 199 | 293 | 387 | 481 | 575 | 669 | 763 | 857 | 383 | |
| 12 | 12 | 106 | 200 | 294 | 388 | 482 | 576 | 670 | 764 | 858 | 384 | |
| 13 | 13 | 107 | 201 | 295 | 389 | 483 | 577 | 671 | 765 | 859 | 385 | |
| 14 | 14 | 108 | 202 | 296 | 390 | 484 | 578 | 672 | 766 | 860 | 386 | |
| 15 | 15 | 109 | 203 | 297 | 391 | 485 | 579 | 673 | 767 | 861 | 387 | |
| 16 | 16 | 110 | 204 | 298 | 392 | 486 | 580 | 674 | 768 | 862 | 388 | |
| 17 | 17 | 111 | 205 | 299 | 393 | 487 | 581 | 675 | 769 | 863 | 389 | |
| 18 | 18 | 112 | 206 | 300 | 394 | 488 | 582 | 676 | 770 | 864 | 390 | |
| 19 | 19 | 113 | 207 | 301 | 395 | 489 | 583 | 677 | 771 | 865 | 391 | |
| 20 | 20 | 114 | 208 | 302 | 396 | 490 | 584 | 678 | 772 | 866 | 392 | |
| 21 | 21 | 115 | 209 | 303 | 397 | 491 | 585 | 679 | 773 | 867 | 465 | |
| 22 | 22 | 116 | 210 | 304 | 398 | 492 | 586 | 680 | 774 | 868 | 466 | |
| 23 | 23 | 117 | 211 | 305 | 399 | 493 | 587 | 681 | 775 | 869 | 467 | |
| 24 | 24 | 118 | 212 | 306 | 400 | 494 | 588 | 682 | 776 | 870 | 468 | |
| 25 | 25 | 119 | 213 | 307 | 401 | 495 | 589 | 683 | 777 | 871 | 469 | |
| 26 | 26 | 120 | 214 | 308 | 402 | 496 | 590 | 684 | 778 | 872 | 470 | |
| 27 | 27 | 121 | 215 | 309 | 403 | 497 | 591 | 685 | 779 | 873 | 471 | |
| 28 | 28 | 122 | 216 | 310 | 404 | 498 | 592 | 686 | 780 | 874 | 472 | |
| 29 | 29 | 123 | 217 | 311 | 405 | 499 | 593 | 687 | 781 | 875 | 473 | |
| 30 | 30 | 124 | 218 | 312 | 406 | 500 | 594 | 688 | 782 | 876 | 474 | |
| 31 | 31 | 125 | 219 | 313 | 407 | 501 | 595 | 689 | 783 | 877 | 475 | |
| 32 | 32 | 126 | 220 | 314 | 408 | 502 | 596 | 690 | 784 | 878 | 476 | |
| 33 | 33 | 127 | 221 | 315 | 409 | 503 | 597 | 691 | 785 | 879 | 477 | |
| 34 | 34 | 128 | 222 | 316 | 410 | 504 | 598 | 692 | 786 | 880 | 478 | |
| 35 | 35 | 129 | 223 | 317 | 411 | 505 | 599 | 693 | 787 | 25 | 479 | |
| 36 | 36 | 130 | 224 | 318 | 412 | 506 | 600 | 694 | 788 | 26 | 480 | |
| 37 | 37 | 131 | 225 | 319 | 413 | 507 | 601 | 695 | 789 | 27 | 553 | |
| 38 | 38 | 132 | 226 | 320 | 414 | 508 | 602 | 696 | 790 | 28 | 554 | |

TABLE 8-continued

Example 3 screening pool design.
94 seq 5 screening pool design

| Screening pool # | Unique pools contained in each screening pool | | | | | | | | | | |
|---|---|---|---|---|---|---|---|---|---|---|---|
| 39 | 39 | 133 | 227 | 321 | 415 | 509 | 603 | 697 | 791 | 29 | 555 |
| 40 | 40 | 134 | 228 | 322 | 416 | 510 | 604 | 698 | 792 | 30 | 556 |
| 41 | 41 | 135 | 229 | 323 | 417 | 511 | 605 | 699 | 793 | 31 | 557 |
| 42 | 42 | 136 | 230 | 324 | 418 | 512 | 606 | 700 | 794 | 32 | 558 |
| 43 | 43 | 137 | 231 | 325 | 419 | 513 | 607 | 701 | 795 | 33 | 559 |
| 44 | 44 | 138 | 232 | 326 | 420 | 514 | 608 | 702 | 796 | 34 | 560 |
| 45 | 45 | 139 | 233 | 327 | 421 | 515 | 609 | 703 | 797 | 35 | 561 |
| 46 | 46 | 140 | 234 | 328 | 422 | 516 | 610 | 704 | 798 | 36 | 562 |
| 47 | 47 | 141 | 235 | 329 | 423 | 517 | 611 | 705 | 799 | 37 | 563 |
| 48 | 48 | 142 | 236 | 330 | 424 | 518 | 612 | 706 | 800 | 38 | 564 |
| 49 | 49 | 143 | 237 | 331 | 425 | 519 | 613 | 707 | 801 | 39 | 565 |
| 50 | 50 | 144 | 238 | 332 | 426 | 520 | 614 | 708 | 802 | 40 | 566 |
| 51 | 51 | 145 | 239 | 333 | 427 | 521 | 615 | 709 | 803 | 113 | 567 |
| 52 | 52 | 146 | 240 | 334 | 428 | 522 | 616 | 710 | 804 | 114 | 568 |
| 53 | 53 | 147 | 241 | 335 | 429 | 523 | 617 | 711 | 805 | 115 | 641 |
| 54 | 54 | 148 | 242 | 336 | 430 | 524 | 618 | 712 | 806 | 116 | 642 |
| 55 | 55 | 149 | 243 | 337 | 431 | 525 | 619 | 713 | 807 | 117 | 643 |
| 56 | 56 | 150 | 244 | 338 | 432 | 526 | 620 | 714 | 808 | 118 | 644 |
| 57 | 57 | 151 | 245 | 339 | 433 | 527 | 621 | 715 | 809 | 119 | 645 |
| 58 | 58 | 152 | 246 | 340 | 434 | 528 | 622 | 716 | 810 | 120 | 646 |
| 59 | 59 | 153 | 247 | 341 | 435 | 529 | 623 | 717 | 811 | 121 | 647 |
| 60 | 60 | 154 | 248 | 342 | 436 | 530 | 624 | 718 | 812 | 122 | 648 |
| 61 | 61 | 155 | 249 | 343 | 437 | 531 | 625 | 719 | 813 | 123 | 649 |
| 62 | 62 | 156 | 250 | 344 | 438 | 532 | 626 | 720 | 814 | 124 | 650 |
| 63 | 63 | 157 | 251 | 345 | 439 | 533 | 627 | 721 | 815 | 125 | 651 |
| 64 | 64 | 158 | 252 | 346 | 440 | 534 | 628 | 722 | 816 | 126 | 652 |
| 65 | 65 | 159 | 253 | 347 | 441 | 535 | 629 | 723 | 817 | 127 | 653 |
| 66 | 66 | 160 | 254 | 348 | 442 | 536 | 630 | 724 | 818 | 128 | 654 |
| 67 | 67 | 161 | 255 | 349 | 443 | 537 | 631 | 725 | 819 | 201 | 655 |
| 68 | 68 | 162 | 256 | 350 | 444 | 538 | 632 | 726 | 820 | 202 | 656 |
| 69 | 69 | 163 | 257 | 351 | 445 | 539 | 633 | 727 | 821 | 203 | 729 |
| 70 | 70 | 164 | 258 | 352 | 446 | 540 | 634 | 728 | 822 | 204 | 730 |
| 71 | 71 | 165 | 259 | 353 | 447 | 541 | 635 | 729 | 823 | 205 | 731 |
| 72 | 72 | 166 | 260 | 354 | 448 | 542 | 636 | 730 | 824 | 206 | 732 |
| 73 | 73 | 167 | 261 | 355 | 449 | 543 | 637 | 731 | 825 | 207 | 733 |
| 74 | 74 | 168 | 262 | 356 | 450 | 544 | 638 | 732 | 826 | 208 | 734 |
| 75 | 75 | 169 | 263 | 357 | 451 | 545 | 639 | 733 | 827 | 209 | 735 |
| 76 | 76 | 170 | 264 | 358 | 452 | 546 | 640 | 734 | 828 | 210 | 736 |
| 77 | 77 | 171 | 265 | 359 | 453 | 547 | 641 | 735 | 829 | 211 | 737 |
| 78 | 78 | 172 | 266 | 360 | 454 | 548 | 642 | 736 | 830 | 212 | 738 |
| 79 | 79 | 173 | 267 | 361 | 455 | 549 | 643 | 737 | 831 | 213 | 739 |
| 80 | 80 | 174 | 268 | 362 | 456 | 550 | 644 | 738 | 832 | 214 | 740 |
| 81 | 81 | 175 | 269 | 363 | 457 | 551 | 645 | 739 | 833 | 215 | 741 |
| 82 | 82 | 176 | 270 | 364 | 458 | 552 | 646 | 740 | 834 | 216 | 742 |
| 83 | 83 | 177 | 271 | 365 | 459 | 553 | 647 | 741 | 835 | 289 | 743 |
| 84 | 84 | 178 | 272 | 366 | 460 | 554 | 648 | 742 | 836 | 290 | 744 |
| 85 | 85 | 179 | 273 | 367 | 461 | 555 | 649 | 743 | 837 | 291 | 817 |
| 86 | 86 | 180 | 274 | 368 | 462 | 556 | 650 | 744 | 838 | 292 | 818 |
| 87 | 87 | 181 | 275 | 369 | 463 | 557 | 651 | 745 | 839 | 293 | 819 |
| 88 | 88 | 182 | 276 | 370 | 464 | 558 | 652 | 746 | 840 | 294 | 820 |
| 89 | 89 | 183 | 277 | 371 | 465 | 559 | 653 | 747 | 841 | 295 | 821 |
| 90 | 90 | 184 | 278 | 372 | 466 | 560 | 654 | 748 | 842 | 296 | 822 |
| 91 | 91 | 185 | 279 | 373 | 467 | 561 | 655 | 749 | 843 | 297 | 823 |
| 92 | 92 | 186 | 280 | 374 | 468 | 562 | 656 | 750 | 844 | 298 | 824 |
| 93 | 93 | 187 | 281 | 375 | 469 | 563 | 657 | 751 | 845 | 299 | 825 |
| 94 | 94 | 188 | 282 | 376 | 470 | 564 | 658 | 752 | 846 | 300 | 826 |

TABLE 9

Example 4 screening pool design.
94 seq 4 & SP screening pool design

| Screening pool # | Unique pools contained in each screening pool | | | | | | | | | | |
|---|---|---|---|---|---|---|---|---|---|---|---|
| 1 | 1 | 85 | 169 | 253 | 337 | 421 | 505 | 589 | 673 | 757 | 841 |
| 2 | 2 | 86 | 170 | 254 | 338 | 422 | 506 | 590 | 674 | 758 | 842 |
| 3 | 3 | 87 | 171 | 255 | 339 | 423 | 507 | 591 | 675 | 759 | 843 |
| 4 | 4 | 88 | 172 | 256 | 340 | 424 | 508 | 592 | 676 | 760 | 844 |

TABLE 9-continued

Example 4 screening pool design.
94 seq 4 & SP screening pool design

| Screening pool # | Unique pools contained in each screening pool | | | | | | | | | | |
|---|---|---|---|---|---|---|---|---|---|---|---|
| 5  | 5  | 89  | 173 | 257 | 341 | 425 | 509 | 593 | 677 | 761 | 845 |
| 6  | 6  | 90  | 174 | 258 | 342 | 426 | 510 | 594 | 678 | 762 | 846 |
| 7  | 7  | 91  | 175 | 259 | 343 | 427 | 511 | 595 | 679 | 763 | 847 |
| 8  | 8  | 92  | 176 | 260 | 344 | 428 | 512 | 596 | 680 | 764 | 848 |
| 9  | 9  | 93  | 177 | 261 | 345 | 429 | 513 | 597 | 681 | 765 | 849 |
| 10 | 10 | 94  | 178 | 262 | 346 | 430 | 514 | 598 | 682 | 766 | 850 |
| 11 | 11 | 95  | 179 | 263 | 347 | 431 | 515 | 599 | 683 | 767 | 851 |
| 12 | 12 | 96  | 180 | 264 | 348 | 432 | 516 | 600 | 684 | 768 | 852 |
| 13 | 13 | 97  | 181 | 265 | 349 | 433 | 517 | 601 | 685 | 769 | 853 |
| 14 | 14 | 98  | 182 | 266 | 350 | 434 | 518 | 602 | 686 | 770 | 854 |
| 15 | 15 | 99  | 183 | 267 | 351 | 435 | 519 | 603 | 687 | 771 | 855 |
| 16 | 16 | 100 | 184 | 268 | 352 | 436 | 520 | 604 | 688 | 772 | 856 |
| 17 | 17 | 101 | 185 | 269 | 353 | 437 | 521 | 605 | 689 | 773 | 857 |
| 18 | 18 | 102 | 186 | 270 | 354 | 438 | 522 | 606 | 690 | 774 | 858 |
| 19 | 19 | 103 | 187 | 271 | 355 | 439 | 523 | 607 | 691 | 775 | 859 |
| 20 | 20 | 104 | 188 | 272 | 356 | 440 | 524 | 608 | 692 | 776 | 860 |
| 21 | 21 | 105 | 189 | 273 | 357 | 441 | 525 | 609 | 693 | 777 | 861 |
| 22 | 22 | 106 | 190 | 274 | 358 | 442 | 526 | 610 | 694 | 778 | 862 |
| 23 | 23 | 107 | 191 | 275 | 359 | 443 | 527 | 611 | 695 | 779 | 863 |
| 24 | 24 | 108 | 192 | 276 | 360 | 444 | 528 | 612 | 696 | 780 | 864 |
| 25 | 25 | 109 | 193 | 277 | 361 | 445 | 529 | 613 | 697 | 781 | 865 |
| 26 | 26 | 110 | 194 | 278 | 362 | 446 | 530 | 614 | 698 | 782 | 866 |
| 27 | 27 | 111 | 195 | 279 | 363 | 447 | 531 | 615 | 699 | 783 | 867 |
| 28 | 28 | 112 | 196 | 280 | 364 | 448 | 532 | 616 | 700 | 784 | 868 |
| 29 | 29 | 113 | 197 | 281 | 365 | 449 | 533 | 617 | 701 | 785 | 869 |
| 30 | 30 | 114 | 198 | 282 | 366 | 450 | 534 | 618 | 702 | 786 | 870 |
| 31 | 31 | 115 | 199 | 283 | 367 | 451 | 535 | 619 | 703 | 787 | 871 |
| 32 | 32 | 116 | 200 | 284 | 368 | 452 | 536 | 620 | 704 | 788 | 872 |
| 33 | 33 | 117 | 201 | 285 | 369 | 453 | 537 | 621 | 705 | 789 | 873 |
| 34 | 34 | 118 | 202 | 286 | 370 | 454 | 538 | 622 | 706 | 790 | 874 |
| 35 | 35 | 119 | 203 | 287 | 371 | 455 | 539 | 623 | 707 | 791 | 875 |
| 36 | 36 | 120 | 204 | 288 | 372 | 456 | 540 | 624 | 708 | 792 | 876 |
| 37 | 37 | 121 | 205 | 289 | 373 | 457 | 541 | 625 | 709 | 793 | 877 |
| 38 | 38 | 122 | 206 | 290 | 374 | 458 | 542 | 626 | 710 | 794 | 878 |
| 39 | 39 | 123 | 207 | 291 | 375 | 459 | 543 | 627 | 711 | 795 | 879 |
| 40 | 40 | 124 | 208 | 292 | 376 | 460 | 544 | 628 | 712 | 796 | 880 |
| 41 | 41 | 125 | 209 | 293 | 377 | 461 | 545 | 629 | 713 | 797 |     |
| 42 | 42 | 126 | 210 | 294 | 378 | 462 | 546 | 630 | 714 | 798 |     |
| 43 | 43 | 127 | 211 | 295 | 379 | 463 | 547 | 631 | 715 | 799 |     |
| 44 | 44 | 128 | 212 | 296 | 380 | 464 | 548 | 632 | 716 | 800 |     |
| 45 | 45 | 129 | 213 | 297 | 381 | 465 | 549 | 633 | 717 | 801 |     |
| 46 | 46 | 130 | 214 | 298 | 382 | 466 | 550 | 634 | 718 | 802 |     |
| 47 | 47 | 131 | 215 | 299 | 383 | 467 | 551 | 635 | 719 | 803 |     |
| 48 | 48 | 132 | 216 | 300 | 384 | 468 | 552 | 636 | 720 | 804 |     |
| 49 | 49 | 133 | 217 | 301 | 385 | 469 | 553 | 637 | 721 | 805 |     |
| 50 | 50 | 134 | 218 | 302 | 386 | 470 | 554 | 638 | 722 | 806 |     |
| 51 | 51 | 135 | 219 | 303 | 387 | 471 | 555 | 639 | 723 | 807 |     |
| 52 | 52 | 136 | 220 | 304 | 388 | 472 | 556 | 640 | 724 | 808 |     |
| 53 | 53 | 137 | 221 | 305 | 389 | 473 | 557 | 641 | 725 | 809 |     |
| 54 | 54 | 138 | 222 | 306 | 390 | 474 | 558 | 642 | 726 | 810 |     |
| 55 | 55 | 139 | 223 | 307 | 391 | 475 | 559 | 643 | 727 | 811 |     |
| 56 | 56 | 140 | 224 | 308 | 392 | 476 | 560 | 644 | 728 | 812 |     |
| 57 | 57 | 141 | 225 | 309 | 393 | 477 | 561 | 645 | 729 | 813 |     |
| 58 | 58 | 142 | 226 | 310 | 394 | 478 | 562 | 646 | 730 | 814 |     |
| 59 | 59 | 143 | 227 | 311 | 395 | 479 | 563 | 647 | 731 | 815 |     |
| 60 | 60 | 144 | 228 | 312 | 396 | 480 | 564 | 648 | 732 | 816 |     |
| 61 | 61 | 145 | 229 | 313 | 397 | 481 | 565 | 649 | 733 | 817 |     |
| 62 | 62 | 146 | 230 | 314 | 398 | 482 | 566 | 650 | 734 | 818 |     |
| 63 | 63 | 147 | 231 | 315 | 399 | 483 | 567 | 651 | 735 | 819 |     |
| 64 | 64 | 148 | 232 | 316 | 400 | 484 | 568 | 652 | 736 | 820 |     |
| 65 | 65 | 149 | 233 | 317 | 401 | 485 | 569 | 653 | 737 | 821 |     |
| 66 | 66 | 150 | 234 | 318 | 402 | 486 | 570 | 654 | 738 | 822 |     |
| 67 | 67 | 151 | 235 | 319 | 403 | 487 | 571 | 655 | 739 | 823 |     |
| 68 | 68 | 152 | 236 | 320 | 404 | 488 | 572 | 656 | 740 | 824 |     |
| 69 | 69 | 153 | 237 | 321 | 405 | 489 | 573 | 657 | 741 | 825 |     |
| 70 | 70 | 154 | 238 | 322 | 406 | 490 | 574 | 658 | 742 | 826 |     |
| 71 | 71 | 155 | 239 | 323 | 407 | 491 | 575 | 659 | 743 | 827 |     |
| 72 | 72 | 156 | 240 | 324 | 408 | 492 | 576 | 660 | 744 | 828 |     |
| 73 | 73 | 157 | 241 | 325 | 409 | 493 | 577 | 661 | 745 | 829 |     |
| 74 | 74 | 158 | 242 | 326 | 410 | 494 | 578 | 662 | 746 | 830 |     |
| 75 | 75 | 159 | 243 | 327 | 411 | 495 | 579 | 663 | 747 | 831 |     |
| 76 | 76 | 160 | 244 | 328 | 412 | 496 | 580 | 664 | 748 | 832 |     |
| 77 | 77 | 161 | 245 | 329 | 413 | 497 | 581 | 665 | 749 | 833 |     |

TABLE 9-continued

Example 4 screening pool design.
94 seq 4 & SP screening pool design

| Screening pool # | Unique pools contained in each screening pool | | | | | | | | | | | | | | |
|---|---|---|---|---|---|---|---|---|---|---|---|---|---|---|---|
| 78 | 78 | 162 | 246 | 330 | 414 | 498 | 582 | 666 | 750 | 834 | | | | | |
| 79 | 79 | 163 | 247 | 331 | 415 | 499 | 583 | 667 | 751 | 835 | | | | | |
| 80 | 80 | 164 | 248 | 332 | 416 | 500 | 584 | 668 | 752 | 836 | | | | | |
| 81 | 81 | 165 | 249 | 333 | 417 | 501 | 585 | 669 | 753 | 837 | | | | | |
| 82 | 82 | 166 | 250 | 334 | 418 | 502 | 586 | 670 | 754 | 838 | | | | | |
| 83 | 83 | 167 | 251 | 335 | 419 | 503 | 587 | 671 | 755 | 839 | | | | | |
| 84 | 84 | 168 | 252 | 336 | 420 | 504 | 588 | 672 | 756 | 840 | | | | | |
| 85 | 25 | 26 | 27 | 28 | 29 | 30 | 31 | 32 | 33 | 34 | 35 | 36 | 37 | 38 | 39 | 40 |
| 86 | 113 | 114 | 115 | 116 | 117 | 118 | 119 | 120 | 121 | 122 | 123 | 124 | 125 | 126 | 127 | 128 |
| 87 | 201 | 202 | 203 | 204 | 205 | 206 | 207 | 208 | 209 | 210 | 211 | 212 | 213 | 214 | 215 | 216 |
| 88 | 289 | 290 | 291 | 292 | 293 | 294 | 295 | 296 | 297 | 298 | 299 | 300 | 301 | 302 | 303 | 304 |
| 89 | 377 | 378 | 379 | 380 | 381 | 382 | 383 | 384 | 385 | 386 | 387 | 388 | 389 | 390 | 391 | 392 |
| 90 | 465 | 466 | 467 | 468 | 469 | 470 | 471 | 472 | 473 | 474 | 475 | 476 | 477 | 478 | 479 | 480 |
| 91 | 553 | 554 | 555 | 556 | 557 | 558 | 559 | 560 | 561 | 562 | 563 | 564 | 565 | 566 | 567 | 568 |
| 92 | 641 | 642 | 643 | 644 | 645 | 646 | 647 | 648 | 649 | 650 | 651 | 652 | 653 | 654 | 655 | 656 |
| 93 | 729 | 730 | 731 | 732 | 733 | 734 | 735 | 736 | 737 | 738 | 739 | 740 | 741 | 742 | 743 | 744 |
| 94 | 817 | 818 | 819 | 820 | 821 | 822 | 823 | 824 | 825 | 826 | 827 | 828 | 829 | 830 | 831 | 832 |

TABLE 10

Example 5 screening pool design.
55 seq 4 & SP screening pool design

| Screening pool # | Unique pools contained in each screening pool | | | | | | | | | |
|---|---|---|---|---|---|---|---|---|---|---|
| 1 1 | 1 | 46 | 91 | 136 | 181 | 226 | 271 | 316 | 361 | 406 |
| 2 | 2 | 47 | 92 | 137 | 182 | 227 | 272 | 317 | 362 | 407 |
| 3 | 3 | 48 | 93 | 138 | 183 | 228 | 273 | 318 | 363 | 408 |
| 4 | 4 | 49 | 94 | 139 | 184 | 229 | 274 | 319 | 364 | 409 |
| 5 | 5 | 50 | 95 | 140 | 185 | 230 | 275 | 320 | 365 | 410 |
| 6 | 6 | 51 | 96 | 141 | 186 | 231 | 276 | 321 | 366 | 411 |
| 7 | 7 | 52 | 97 | 142 | 187 | 232 | 277 | 322 | 367 | 412 |
| 8 | 8 | 53 | 98 | 143 | 188 | 233 | 278 | 323 | 368 | 413 |
| 9 | 9 | 54 | 99 | 144 | 189 | 234 | 279 | 324 | 369 | 414 |
| 10 | 10 | 55 | 100 | 145 | 190 | 235 | 280 | 325 | 370 | 415 |
| 11 | 11 | 56 | 101 | 146 | 191 | 236 | 281 | 326 | 371 | 416 |
| 12 | 12 | 57 | 102 | 147 | 192 | 237 | 282 | 327 | 372 | 417 |
| 13 | 13 | 58 | 103 | 148 | 193 | 238 | 283 | 328 | 373 | 418 |
| 14 | 14 | 59 | 104 | 149 | 194 | 239 | 284 | 329 | 374 | 419 |
| 15 | 15 | 60 | 105 | 150 | 195 | 240 | 285 | 330 | 375 | 420 |
| 16 | 16 | 61 | 106 | 151 | 196 | 241 | 286 | 331 | 376 | 421 |
| 17 | 17 | 62 | 107 | 152 | 197 | 242 | 287 | 332 | 377 | 422 |
| 18 | 18 | 63 | 108 | 153 | 198 | 243 | 288 | 333 | 378 | 423 |
| 19 | 19 | 64 | 109 | 154 | 199 | 244 | 289 | 334 | 379 | 424 |
| 20 | 20 | 65 | 110 | 155 | 200 | 245 | 290 | 335 | 380 | 425 |
| 21 | 21 | 66 | 111 | 156 | 201 | 246 | 291 | 336 | 381 | 426 |
| 22 | 22 | 67 | 112 | 157 | 202 | 247 | 292 | 337 | 382 | 427 |
| 23 | 23 | 68 | 113 | 158 | 203 | 248 | 293 | 338 | 383 | 428 |
| 24 | 24 | 69 | 114 | 159 | 204 | 249 | 294 | 339 | 384 | 429 |
| 25 | 25 | 70 | 115 | 160 | 205 | 250 | 295 | 340 | 385 | 430 |
| 26 | 26 | 71 | 116 | 161 | 206 | 251 | 296 | 341 | 386 | 431 |
| 27 | 27 | 72 | 117 | 162 | 207 | 252 | 297 | 342 | 387 | 432 |
| 28 | 28 | 73 | 118 | 163 | 208 | 253 | 298 | 343 | 388 | 433 |
| 29 | 29 | 74 | 119 | 164 | 209 | 254 | 299 | 344 | 389 | 434 |
| 30 | 30 | 75 | 120 | 165 | 210 | 255 | 300 | 345 | 390 | 435 |
| 31 | 31 | 76 | 121 | 166 | 211 | 256 | 301 | 346 | 391 | 436 |
| 32 | 32 | 77 | 122 | 167 | 212 | 257 | 302 | 347 | 392 | 437 |
| 33 | 33 | 78 | 123 | 168 | 213 | 258 | 303 | 348 | 393 | 438 |
| 34 | 34 | 79 | 124 | 169 | 214 | 259 | 304 | 349 | 394 | 439 |
| 35 | 35 | 80 | 125 | 170 | 215 | 260 | 305 | 350 | 395 | 440 |
| 36 | 36 | 81 | 126 | 171 | 216 | 261 | 306 | 351 | 396 | 441 |
| 37 | 37 | 82 | 127 | 172 | 217 | 262 | 307 | 352 | 397 | 442 |
| 38 | 38 | 83 | 128 | 173 | 218 | 263 | 308 | 353 | 398 | 443 |
| 39 | 39 | 84 | 129 | 174 | 219 | 264 | 309 | 354 | 399 | 444 |
| 40 | 40 | 85 | 130 | 175 | 220 | 265 | 310 | 355 | 400 | 445 |
| 41 | 41 | 86 | 131 | 176 | 221 | 266 | 311 | 356 | 401 | 446 |
| 42 | 42 | 87 | 132 | 177 | 222 | 267 | 312 | 357 | 402 | 447 |
| 43 | 43 | 88 | 133 | 178 | 223 | 268 | 313 | 358 | 403 | 448 |
| 44 | 44 | 89 | 134 | 179 | 224 | 269 | 314 | 359 | 404 | 449 |

TABLE 10-continued

Example 5 screening pool design.
55 seq 4 & SP screening pool design

| 45 | 45  | 90  | 135 | 180 | 225 | 270 | 315 | 360 | 405 | 450 |
|----|-----|-----|-----|-----|-----|-----|-----|-----|-----|-----|
| 46 | 25  | 26  | 27  | 28  | 29  | 30  | 31  | 32  | 33  | 34  |
| 47 | 113 | 114 | 115 | 116 | 117 | 118 | 119 | 120 | 121 | 122 |
| 48 | 201 | 202 | 203 | 204 | 205 | 206 | 207 | 208 | 209 | 210 |
| 49 | 289 | 290 | 291 | 292 | 293 | 294 | 295 | 296 | 297 | 298 |
| 50 | 377 | 378 | 379 | 380 | 381 | 382 | 383 | 384 | 385 | 386 |
| 51 | 465 | 466 | 467 | 468 | 469 | 470 | 471 | 472 | 473 | 474 |
| 52 | 553 | 554 | 555 | 556 | 557 | 558 | 559 | 560 | 561 | 562 |
| 53 | 641 | 642 | 643 | 644 | 645 | 646 | 647 | 648 | 649 | 650 |
| 54 | 729 | 730 | 731 | 732 | 733 | 734 | 735 | 736 | 737 | 738 |
| 55 | 817 | 818 | 819 | 820 | 821 | 822 | 823 | 824 | 825 | 826 |

| Screening pool # | Unique pools contained in each screening pool | | | | | | | | | |
|----|-----|-----|-----|-----|-----|-----|-----|-----|-----|-----|
| 1  | 451 | 496 | 541 | 586 | 631 | 676 | 721 | 766 | 811 | 856 |
| 2  | 452 | 497 | 542 | 587 | 632 | 677 | 722 | 767 | 812 | 857 |
| 3  | 453 | 498 | 543 | 588 | 633 | 678 | 723 | 768 | 813 | 858 |
| 4  | 454 | 499 | 544 | 589 | 634 | 679 | 724 | 769 | 814 | 859 |
| 5  | 455 | 500 | 545 | 590 | 635 | 680 | 725 | 770 | 815 | 860 |
| 6  | 456 | 501 | 546 | 591 | 636 | 681 | 726 | 771 | 816 | 861 |
| 7  | 457 | 502 | 547 | 592 | 637 | 682 | 727 | 772 | 817 | 862 |
| 8  | 458 | 503 | 548 | 593 | 638 | 683 | 728 | 773 | 818 | 863 |
| 9  | 459 | 504 | 549 | 594 | 639 | 684 | 729 | 774 | 819 | 864 |
| 10 | 460 | 505 | 550 | 595 | 640 | 685 | 730 | 775 | 820 | 865 |
| 11 | 461 | 506 | 551 | 596 | 641 | 686 | 731 | 776 | 821 | 866 |
| 12 | 462 | 507 | 552 | 597 | 642 | 687 | 732 | 777 | 822 | 867 |
| 13 | 463 | 508 | 553 | 598 | 643 | 688 | 733 | 778 | 823 | 868 |
| 14 | 464 | 509 | 554 | 599 | 644 | 689 | 734 | 779 | 824 | 869 |
| 15 | 465 | 510 | 555 | 600 | 645 | 690 | 735 | 780 | 825 | 870 |
| 16 | 466 | 511 | 556 | 601 | 646 | 691 | 736 | 781 | 826 | 871 |
| 17 | 467 | 512 | 557 | 602 | 647 | 692 | 737 | 782 | 827 | 872 |
| 18 | 468 | 513 | 558 | 603 | 648 | 693 | 738 | 783 | 828 | 873 |
| 19 | 469 | 514 | 559 | 604 | 649 | 694 | 739 | 784 | 829 | 874 |
| 20 | 470 | 515 | 560 | 605 | 650 | 695 | 740 | 785 | 830 | 875 |
| 21 | 471 | 516 | 561 | 606 | 651 | 696 | 741 | 786 | 831 | 876 |
| 22 | 472 | 517 | 562 | 607 | 652 | 697 | 742 | 787 | 832 | 877 |
| 23 | 473 | 518 | 563 | 608 | 653 | 698 | 743 | 788 | 833 | 878 |
| 24 | 474 | 519 | 564 | 609 | 654 | 699 | 744 | 789 | 834 | 879 |
| 25 | 475 | 520 | 565 | 610 | 655 | 700 | 745 | 790 | 835 | 880 |
| 26 | 476 | 521 | 566 | 611 | 656 | 701 | 746 | 791 | 836 |     |
| 27 | 477 | 522 | 567 | 612 | 657 | 702 | 747 | 792 | 837 |     |
| 28 | 478 | 523 | 568 | 613 | 658 | 703 | 748 | 793 | 838 |     |
| 29 | 479 | 524 | 569 | 614 | 659 | 704 | 749 | 794 | 839 |     |
| 30 | 480 | 525 | 570 | 615 | 660 | 705 | 750 | 795 | 840 |     |
| 31 | 481 | 526 | 571 | 616 | 661 | 706 | 751 | 796 | 841 |     |
| 32 | 482 | 527 | 572 | 617 | 662 | 707 | 752 | 797 | 842 |     |
| 33 | 483 | 528 | 573 | 618 | 663 | 708 | 753 | 798 | 843 |     |
| 34 | 484 | 529 | 574 | 619 | 664 | 709 | 754 | 799 | 844 |     |
| 35 | 485 | 530 | 575 | 620 | 665 | 710 | 755 | 800 | 845 |     |
| 36 | 486 | 531 | 576 | 621 | 666 | 711 | 756 | 801 | 846 |     |
| 37 | 487 | 532 | 577 | 622 | 667 | 712 | 757 | 802 | 847 |     |
| 38 | 488 | 533 | 578 | 623 | 668 | 713 | 758 | 803 | 848 |     |
| 39 | 489 | 534 | 579 | 624 | 669 | 714 | 759 | 804 | 849 |     |
| 40 | 490 | 535 | 580 | 625 | 670 | 715 | 760 | 805 | 850 |     |
| 41 | 491 | 536 | 581 | 626 | 671 | 716 | 761 | 806 | 851 |     |
| 42 | 492 | 537 | 582 | 627 | 672 | 717 | 762 | 807 | 852 |     |
| 43 | 493 | 538 | 583 | 628 | 673 | 718 | 763 | 808 | 853 |     |
| 44 | 494 | 539 | 584 | 629 | 674 | 719 | 764 | 809 | 854 |     |
| 45 | 495 | 540 | 585 | 630 | 675 | 720 | 765 | 810 | 855 |     |
| 46 | 35  | 36  | 37  | 38  | 39  | 40  |     |     |     |     |
| 47 | 123 | 124 | 125 | 126 | 127 | 128 |     |     |     |     |
| 48 | 211 | 212 | 213 | 214 | 215 | 216 |     |     |     |     |
| 49 | 299 | 300 | 301 | 302 | 303 | 304 |     |     |     |     |
| 50 | 387 | 388 | 389 | 390 | 391 | 392 |     |     |     |     |
| 51 | 475 | 476 | 477 | 478 | 479 | 480 |     |     |     |     |
| 52 | 563 | 564 | 565 | 566 | 567 | 568 |     |     |     |     |
| 53 | 651 | 652 | 653 | 654 | 655 | 656 |     |     |     |     |
| 54 | 739 | 740 | 741 | 742 | 743 | 744 |     |     |     |     |
| 55 | 827 | 828 | 829 | 830 | 831 | 832 |     |     |     |     |

TABLE 11

Example 5 screening pool design.
45 seq 5 screening pool design

| Screening pool # | Unique pools contained in each screening pool | | | | | | | | | | | |
|---|---|---|---|---|---|---|---|---|---|---|---|---|
| 1 | 1 | 46 | 91 | 136 | 181 | 226 | 271 | 316 | 361 | 406 | 451 | 496 | 541 |
| 2 | 2 | 47 | 92 | 137 | 182 | 227 | 272 | 317 | 362 | 407 | 452 | 497 | 542 |
| 3 | 3 | 48 | 93 | 138 | 183 | 228 | 273 | 318 | 363 | 408 | 453 | 498 | 543 |
| 4 | 4 | 49 | 94 | 139 | 184 | 229 | 274 | 319 | 364 | 409 | 454 | 499 | 544 |
| 5 | 5 | 50 | 95 | 140 | 185 | 230 | 275 | 320 | 365 | 410 | 455 | 500 | 545 |
| 6 | 6 | 51 | 96 | 141 | 186 | 231 | 276 | 321 | 366 | 411 | 456 | 501 | 546 |
| 7 | 7 | 52 | 97 | 142 | 187 | 232 | 277 | 322 | 367 | 412 | 457 | 502 | 547 |
| 8 | 8 | 53 | 98 | 143 | 188 | 233 | 278 | 323 | 368 | 413 | 458 | 503 | 548 |
| 9 | 9 | 54 | 99 | 144 | 189 | 234 | 279 | 324 | 369 | 414 | 459 | 504 | 549 |
| 10 | 10 | 55 | 100 | 145 | 190 | 235 | 280 | 325 | 370 | 415 | 460 | 505 | 550 |
| 11 | 11 | 56 | 101 | 146 | 191 | 236 | 281 | 326 | 371 | 416 | 461 | 506 | 551 |
| 12 | 12 | 57 | 102 | 147 | 192 | 237 | 282 | 327 | 372 | 417 | 462 | 507 | 552 |
| 13 | 13 | 58 | 103 | 148 | 193 | 238 | 283 | 328 | 373 | 418 | 463 | 508 | 553 |
| 14 | 14 | 59 | 104 | 149 | 194 | 239 | 284 | 329 | 374 | 419 | 464 | 509 | 554 |
| 15 | 15 | 60 | 105 | 150 | 195 | 240 | 285 | 330 | 375 | 420 | 465 | 510 | 555 |
| 16 | 16 | 61 | 106 | 151 | 196 | 241 | 286 | 331 | 376 | 421 | 466 | 511 | 556 |
| 17 | 17 | 62 | 107 | 152 | 197 | 242 | 287 | 332 | 377 | 422 | 467 | 512 | 557 |
| 18 | 18 | 63 | 108 | 153 | 198 | 243 | 288 | 333 | 378 | 423 | 468 | 513 | 558 |
| 19 | 19 | 64 | 109 | 154 | 199 | 244 | 289 | 334 | 379 | 424 | 469 | 514 | 559 |
| 20 | 20 | 65 | 110 | 155 | 200 | 245 | 290 | 335 | 380 | 425 | 470 | 515 | 560 |
| 21 | 21 | 66 | 111 | 156 | 201 | 246 | 291 | 336 | 381 | 426 | 471 | 516 | 561 |
| 22 | 22 | 67 | 112 | 157 | 202 | 247 | 292 | 337 | 382 | 427 | 472 | 517 | 562 |
| 23 | 23 | 68 | 113 | 158 | 203 | 248 | 293 | 338 | 383 | 428 | 473 | 518 | 563 |
| 24 | 24 | 69 | 114 | 159 | 204 | 249 | 294 | 339 | 384 | 429 | 474 | 519 | 564 |
| 25 | 25 | 70 | 115 | 160 | 205 | 250 | 295 | 340 | 385 | 430 | 475 | 520 | 565 |
| 26 | 26 | 71 | 116 | 161 | 206 | 251 | 296 | 341 | 386 | 431 | 476 | 521 | 566 |
| 27 | 27 | 72 | 117 | 162 | 207 | 252 | 297 | 342 | 387 | 432 | 477 | 522 | 567 |
| 28 | 28 | 73 | 118 | 163 | 208 | 253 | 298 | 343 | 388 | 433 | 478 | 523 | 568 |
| 29 | 29 | 74 | 119 | 164 | 209 | 254 | 299 | 344 | 389 | 434 | 479 | 524 | 569 |
| 30 | 30 | 75 | 120 | 165 | 210 | 255 | 300 | 345 | 390 | 435 | 480 | 525 | 570 |
| 31 | 31 | 76 | 121 | 166 | 211 | 256 | 301 | 346 | 391 | 436 | 481 | 526 | 571 |
| 32 | 32 | 77 | 122 | 167 | 212 | 257 | 302 | 347 | 392 | 437 | 482 | 527 | 572 |
| 33 | 33 | 78 | 123 | 168 | 213 | 258 | 303 | 348 | 393 | 438 | 483 | 528 | 573 |
| 34 | 34 | 79 | 124 | 169 | 214 | 259 | 304 | 349 | 394 | 439 | 484 | 529 | 574 |
| 35 | 35 | 80 | 125 | 170 | 215 | 260 | 305 | 350 | 395 | 440 | 485 | 530 | 575 |
| 36 | 36 | 81 | 126 | 171 | 216 | 261 | 306 | 351 | 396 | 441 | 486 | 531 | 576 |
| 37 | 37 | 82 | 127 | 172 | 217 | 262 | 307 | 352 | 397 | 442 | 487 | 532 | 577 |
| 38 | 38 | 83 | 128 | 173 | 218 | 263 | 308 | 353 | 398 | 443 | 488 | 533 | 578 |
| 39 | 39 | 84 | 129 | 174 | 219 | 264 | 309 | 354 | 399 | 444 | 489 | 534 | 579 |
| 40 | 40 | 85 | 130 | 175 | 220 | 265 | 310 | 355 | 400 | 445 | 490 | 535 | 580 |
| 41 | 41 | 86 | 131 | 176 | 221 | 266 | 311 | 356 | 401 | 446 | 491 | 536 | 581 |
| 42 | 42 | 87 | 132 | 177 | 222 | 267 | 312 | 357 | 402 | 447 | 492 | 537 | 582 |
| 43 | 43 | 88 | 133 | 178 | 223 | 268 | 313 | 358 | 403 | 448 | 493 | 538 | 583 |
| 44 | 44 | 89 | 134 | 179 | 224 | 269 | 314 | 359 | 404 | 449 | 494 | 539 | 584 |
| 45 | 45 | 90 | 135 | 180 | 225 | 270 | 315 | 360 | 405 | 450 | 495 | 540 | 585 |

| Screening pool # | Unique pools contained in each screening pool | | | | | | | | | | | |
|---|---|---|---|---|---|---|---|---|---|---|---|---|
| 1 | 586 | 631 | 676 | 721 | 766 | 811 | 856 | 21 | 194 | 367 | 540 | 713 |
| 2 | 587 | 632 | 677 | 722 | 767 | 812 | 857 | 22 | 195 | 368 | 541 | 714 |
| 3 | 588 | 633 | 678 | 723 | 768 | 813 | 858 | 23 | 196 | 369 | 542 | 715 |
| 4 | 589 | 634 | 679 | 724 | 769 | 814 | 859 | 24 | 197 | 370 | 543 | 716 |
| 5 | 590 | 635 | 680 | 725 | 770 | 815 | 860 | 89 | 198 | 371 | 544 | 717 |
| 6 | 591 | 636 | 681 | 726 | 771 | 816 | 861 | 90 | 199 | 372 | 545 | 718 |
| 7 | 592 | 637 | 682 | 727 | 772 | 817 | 862 | 91 | 200 | 373 | 546 | 719 |
| 8 | 593 | 638 | 683 | 728 | 773 | 818 | 863 | 92 | 265 | 374 | 547 | 720 |
| 9 | 594 | 639 | 684 | 729 | 774 | 819 | 864 | 93 | 266 | 375 | 548 | 721 |
| 10 | 595 | 640 | 685 | 730 | 775 | 820 | 865 | 94 | 267 | 376 | 549 | 722 |
| 11 | 596 | 641 | 686 | 731 | 776 | 821 | 866 | 95 | 268 | 441 | 550 | 723 |
| 12 | 597 | 642 | 687 | 732 | 777 | 822 | 867 | 96 | 269 | 442 | 551 | 724 |
| 13 | 598 | 643 | 688 | 733 | 778 | 823 | 868 | 97 | 270 | 443 | 552 | 725 |
| 14 | 599 | 644 | 689 | 734 | 779 | 824 | 869 | 98 | 271 | 444 | 617 | 726 |
| 15 | 600 | 645 | 690 | 735 | 780 | 825 | 870 | 99 | 272 | 445 | 618 | 727 |
| 16 | 601 | 646 | 691 | 736 | 781 | 826 | 871 | 100 | 273 | 446 | 619 | 728 |
| 17 | 602 | 647 | 692 | 737 | 782 | 827 | 872 | 101 | 274 | 447 | 620 | 793 |
| 18 | 603 | 648 | 693 | 738 | 783 | 828 | 873 | 102 | 275 | 448 | 621 | 794 |
| 19 | 604 | 649 | 694 | 739 | 784 | 829 | 874 | 103 | 276 | 449 | 622 | 795 |
| 20 | 605 | 650 | 695 | 740 | 785 | 830 | 875 | 104 | 277 | 450 | 623 | 796 |
| 21 | 606 | 651 | 696 | 741 | 786 | 831 | 876 | 105 | 278 | 451 | 624 | 797 |
| 22 | 607 | 652 | 697 | 742 | 787 | 832 | 877 | 106 | 279 | 452 | 625 | 798 |
| 23 | 608 | 653 | 698 | 743 | 788 | 833 | 878 | 107 | 280 | 453 | 626 | 799 |
| 24 | 609 | 654 | 699 | 744 | 789 | 834 | 879 | 108 | 281 | 454 | 627 | 800 |
| 25 | 610 | 655 | 700 | 745 | 790 | 835 | 880 | 109 | 282 | 455 | 628 | 801 |

TABLE 11-continued

Example 5 screening pool design.
45 seq 5 screening pool design

| 26 | 611 | 656 | 701 | 746 | 791 | 836 | 1  | 110 | 283 | 456 | 629 | 802 |
| 27 | 612 | 657 | 702 | 747 | 792 | 837 | 2  | 111 | 284 | 457 | 630 | 803 |
| 28 | 613 | 658 | 703 | 748 | 793 | 838 | 3  | 112 | 285 | 458 | 631 | 804 |
| 29 | 614 | 659 | 704 | 749 | 794 | 839 | 4  | 177 | 286 | 459 | 632 | 805 |
| 30 | 615 | 660 | 705 | 750 | 795 | 840 | 5  | 178 | 287 | 460 | 633 | 806 |
| 31 | 616 | 661 | 706 | 751 | 796 | 841 | 6  | 179 | 288 | 461 | 634 | 807 |
| 32 | 617 | 662 | 707 | 752 | 797 | 842 | 7  | 180 | 353 | 462 | 635 | 808 |
| 33 | 618 | 663 | 708 | 753 | 798 | 843 | 8  | 181 | 354 | 463 | 636 | 809 |
| 34 | 619 | 664 | 709 | 754 | 799 | 844 | 9  | 182 | 355 | 464 | 637 | 810 |
| 35 | 620 | 665 | 710 | 755 | 800 | 845 | 10 | 183 | 356 | 529 | 638 | 811 |
| 36 | 621 | 666 | 711 | 756 | 801 | 846 | 11 | 184 | 357 | 530 | 639 | 812 |
| 37 | 622 | 667 | 712 | 757 | 802 | 847 | 12 | 185 | 358 | 531 | 640 | 813 |
| 38 | 623 | 668 | 713 | 758 | 803 | 848 | 13 | 186 | 359 | 532 | 705 | 814 |
| 39 | 624 | 669 | 714 | 759 | 804 | 849 | 14 | 187 | 360 | 533 | 706 | 815 |
| 40 | 625 | 670 | 715 | 760 | 805 | 850 | 15 | 188 | 361 | 534 | 707 | 816 |
| 41 | 626 | 671 | 716 | 761 | 806 | 851 | 16 | 189 | 362 | 535 | 708 |     |
| 42 | 627 | 672 | 717 | 762 | 807 | 852 | 17 | 190 | 363 | 536 | 709 |     |
| 43 | 628 | 673 | 718 | 763 | 808 | 853 | 18 | 191 | 364 | 537 | 710 |     |
| 44 | 629 | 674 | 719 | 764 | 809 | 854 | 19 | 192 | 365 | 538 | 711 |     |
| 45 | 630 | 675 | 720 | 765 | 810 | 855 | 20 | 193 | 366 | 539 | 712 |     |

Tables 8, 9, 10 and 11 shows four of the many specific repooling designs that were tested to demonstrate the utility of this patent.

Tables 12-16 are data showing multiple embodiments of various randomization schemes for pooling a quantification of data loaded into the Matrix Pool Plate (FIG. 5).

TABLE 12

Summary of various screening pool
design unique clone identification.

Pooling Summary with each clone
contained in 4 to 8 unique pools.

| Screening Pool size | design | Total possible instances of clone | Unique clone identification |  |  |  |
|---|---|---|---|---|---|---|
|  |  |  | maximum | −1 | −2 | −3 |
| 30 | rnd 4 | 4 | 86.4% | 13.0% | 0.6% | 0.0% |
| 30 | seq 4 | 4 | 83.7% | 16.0% | 0.3% | 0.0% |
| 45 | rnd 4 | 4 | 88.0% | 11.6% | 0.3% | 0.0% |
| 45 | seq 5 | 5 | 85.1% | 14.3% | 0.6% | 0.0% |
| 55 | seq 4 & SP | 5 | 91.2% | 8.5% | 0.2% | 0.0% |
| 61 | rnd 4 | 4 | 91.9% | 8.0% | 0.1% | 0.0% |
| 61 | seq 4 | 4 | 95.1% | 4.9% | 0.0% | 0.0% |
| 89 | seq & step 8 | 8 | 100.0% | 0.0% | 0.0% | 0.0% |
| 89 | seq 8 | 8 | 100.0% | 0.0% | 0.0% | 0.0% |
| 89 | seq & rnd 8 | 8 | 100.0% | 0.0% | 0.0% | 0.0% |
| 89 | seq 6 | 6 | 100.0% | 0.0% | 0.0% | 0.0% |
| 89 | step 5 | 5 | 100.0% | 0.0% | 0.0% | 0.0% |
| 89 | seq 5 | 5 | 100.0% | 0.0% | 0.0% | 0.0% |
| 89 | rnd 4 | 4 | 94.6% | 5.3% | 0.1% | 0.0% |
| 89 | seq 4 | 4 | 100.0% | 0.0% | 0.0% | 0.0% |
| 94 | seq 4 & SP | 5 | 99.3% | 0.7% | 0.0% | 0.0% |
| 94 | seq 5 | 5 | 96.8% | 3.2% | 0.0% | 0.0% |

TABLE 13

Summary of various screening pool
design unique clone identification.

Possibilities to find one random clone

| Screening Pool size | design | False positives found during identification |  |  |  |  |  |  |  |
|---|---|---|---|---|---|---|---|---|---|
|  |  | <9 | 9–7 | 7–5 | 5–3 | 2 | 1 | 0 | −1 |
| 30 | rnd 4 |  |  |  |  |  |  |  |  |
| 30 | seq 4 |  |  |  |  |  |  |  |  |
| 45 | rnd 4 |  |  |  |  |  |  |  |  |
| 45 | seq 5 | 0% | 0% | 0% | 4% | 3% | 46% | 48% | 4% |
| 55 | seq 4 & SP | 0% | 0% | 0% | 0% | 0% | 43% | 49% | 8% |
| 61 | rnd 4 |  |  |  |  |  |  |  |  |
| 61 | seq 4 |  |  |  |  |  |  |  |  |
| 89 | seq & step 8 | 0% | 0% | 0% | 0% | 0% | 0% | 100% |  |
| 89 | seq 8 | 0% | 0% | 0% | 0% | 0% | 0% | 100% |  |
| 89 | seq & rnd 8 | 0% | 0% | 0% | 0% | 0% | 0% | 100% |  |
| 89 | seq 6 | 0% | 0% | 0% | 0% | 0% | 0% | 100% |  |
| 89 | step 5 | 0% | 0% | 0% | 0% | 0% | 0% | 100% |  |
| 89 | seq 5 | 0% | 0% | 0% | 0% | 0% | 0% | 100% |  |
| 89 | rnd 4 | 0% | 0% | 0% | 0% | 0% | 0% | 95% | 5% |
| 89 | seq 4 | 0% | 0% | 0% | 0% | 0% | 0% | 100% |  |
| 94 | seq 4 & SP | 0% | 0% | 0% | 0% | 0% | 0% | 100% |  |
| 94 | seq 5 | 0% | 0% | 0% | 0% | 0% | 0% | 96% | 4% |

TABLE 14

Summary of various screening pool designs searching for one unique
clone identification.

Possibilities to find one random clone

| Screening Pool size | design | False positives found during identification |  |  |  |  |  |  |  |
|---|---|---|---|---|---|---|---|---|---|
|  |  | <9 | 9–7 | 7–5 | 5–3 | 2 | 1 | 0 | −1 |
| 30 | rnd 4 |  |  |  |  |  |  |  |  |
| 30 | seq 4 |  |  |  |  |  |  |  |  |
| 45 | rnd 4 |  |  |  |  |  |  |  |  |
| 45 | seq 5 | 0% | 0% | 0% | 4% | 3% | 46% | 48% | 4% |
| 55 | seq 4 & SP | 0% | 0% | 0% | 0% | 0% | 43% | 49% | 8% |
| 61 | rnd 4 |  |  |  |  |  |  |  |  |

TABLE 14-continued

Summary of various screening pool designs searching for one unique clone identification.

Possibilities to find one random clone

| Screening Pool size | design | <9 | 9–7 | 7–5 | 5–3 | 2 | 1 | 0 | –1 |
|---|---|---|---|---|---|---|---|---|---|
| 61 | seq 4 | | | | | | | | |
| 89 | seq & step 8 | 0% | 0% | 0% | 0% | 0% | 0% | 100% | |
| 89 | seq 8 | 0% | 0% | 0% | 0% | 0% | 0% | 100% | |
| 89 | seq & rnd 8 | 0% | 0% | 0% | 0% | 0% | 0% | 100% | |
| 89 | seq 6 | 0% | 0% | 0% | 0% | 0% | 0% | 100% | |
| 89 | step 5 | 0% | 0% | 0% | 0% | 0% | 0% | 100% | |
| 89 | seq 5 | 0% | 0% | 0% | 0% | 0% | 0% | 100% | |
| 89 | rnd 4 | 0% | 0% | 0% | 0% | 0% | 0% | 95% | 5% |
| 89 | seq 4 | 0% | 0% | 0% | 0% | 0% | 0% | 100% | |
| 94 | seq 4 & SP | 0% | 0% | 0% | 0% | 0% | 0% | 100% | |
| 94 | seq 5 | 0% | 0% | 0% | 0% | 0% | 0% | 96% | 4% |

TABLE 15

Summary of various screening pool designs searching for two unique clone identifications.
Possibilities to find random sets of 2 unique but similar marker containing clones

| Screening pool | design | 6+ | 5 | 4 | 3 | 2 | 1 | 0 | –1 |
|---|---|---|---|---|---|---|---|---|---|
| 30 | rnd 4 | | | | | | | | |
| 30 | seq 4 | | | | | | | | |
| 45 | rnd 4 | | | | | | | | |
| 45 | seq 5 | 39% | 12% | 11% | 11% | 8% | 10% | 7% | 1% |
| 55 | seq 4 & SP | 15% | 10% | 14% | 24% | 10% | 16% | 8% | 1% |
| 61 | rnd 4 | | | | | | | | |
| 61 | seq 4 | | | | | | | | |
| 89 | seq & step 8 | 4% | 4% | 4% | 6% | 22% | 33% | 21% | 0% |
| 89 | seq 8 | | | | | | | | |
| 89 | seq & rnd 8 | 0% | 0% | 0% | 0% | 2% | 5% | 61% | 29% |
| 89 | seq 6 | | | | | | | | |
| 89 | step 5 | 1% | 1% | 3% | 11% | 14% | 41% | 29% | 0% |
| 89 | seq 5 | 0% | 0% | 1% | 1% | 7% | 22% | 63% | 6% |
| 89 | rnd 4 | 0% | 0% | 1% | 4% | 10% | 20% | 64% | 1% |
| 89 | seq 4 | 1% | 1% | 4% | 5% | 17% | 38% | 34% | 0% |
| 94 | seq 4 & SP | 0% | 0% | 0% | 0% | 5% | 11% | 84% | 0% |
| 94 | seq 5 | 0% | 0% | 0% | 1% | 7% | 20% | 69% | 3% |

TABLE 16

Summary of various screening pool designs searching for three unique clone identifications.

Possibilities to find random sets of 3 unique but similar marker containing clones

| Screening Pool size | design | >15 | 14 | 13 | 12 | 11 | 10 | 9 | 8 | 7 | 6 | 5 | 4 | 3 | 2 | 1 | 0 | –1 | –2 |
|---|---|---|---|---|---|---|---|---|---|---|---|---|---|---|---|---|---|---|---|
| 30 | rnd 4 | | | | | | | | | | | | | | | | | | |
| 30 | seq 4 | | | | | | | | | | | | | | | | | | |
| 45 | rnd 4 | | | | | | | | | | | | | | | | | | |
| 45 | seq 5 | 89% | 0% | 1% | 1% | 0% | 2% | 0% | 2% | 0% | 2% | 0% | 0% | 1% | 0% | 0% | 0% | 0% | 0% |
| 55 | seg 4 & SP | 61% | 8% | 3% | 2% | 2% | 5% | 7% | 1% | 0% | 3% | 3% | 0% | 1% | 1% | 0% | 0% | 0% | 0% |
| 61 | rnd 4 | | | | | | | | | | | | | | | | | | |
| 61 | seq 4 | | | | | | | | | | | | | | | | | | |
| 89 | seg & step 8 | 20% | 4% | 3% | 4% | 3% | 6% | 9% | 10% | 13% | 8% | 9% | 6% | 3% | 1% | 0% | 1% | 0% | 0% |
| 89 | seq 8 | 17% | 4% | 3% | 4% | 14% | 6% | 7% | 6% | 10% | 14% | 8% | 10% | 5% | 0% | 1% | 0% | 1% | 0% |
| 89 | seq & rnd 8 | 2% | 2% | 5% | 5% | 3% | 2% | 11% | 9% | 13% | 14% | 13% | 10% | 6% | 2% | 2% | 1% | 0% | 0% |
| 89 | seq 6 | 0% | 0% | 0% | 0% | 0% | 0% | 0% | 0% | 0% | 2% | 3% | 2% | 7% | 19% | 20% | 27% | 17% | 1% |
| 89 | step 5 | 2% | 2% | 5% | 5% | 3% | 2% | 11% | 9% | 13% | 14% | 13% | 10% | 6% | 2% | 2% | 1% | 0% | 0% |
| 89 | seq 5 | 0% | 0% | 0% | 0% | 0% | 0% | 0% | 1% | 5% | 3% | 7% | 14% | 14% | 16% | 28% | 9% | 3% | 0% |

TABLE 16-continued

Summary of various screening pool designs searching for three unique clone identifications.

| | | Possibilities to find random sets of 3 unique but similar marker containing clones | | | | | | | | | | | | | | | | |
|---|---|---|---|---|---|---|---|---|---|---|---|---|---|---|---|---|---|---|
| Screening | | False positives found during identification | | | | | | | | | | | | | | | | |
| Pool size | design | >15 | 14 | 13 | 12 | 11 | 10 | 9 | 8 | 7 | 6 | 5 | 4 | 3 | 2 | 1 | 0 | −1 | −2 |
| 89 | rnd 4 | 0% | 0% | 0% | 0% | 0% | 0% | 0% | 5% | 5% | 9% | 8% | 13% | 17% | 17% | 19% | 7% | 0% | 0% |
| 89 | seq 4 | 2% | 2% | 1% | 3% | 2% | 2% | 10% | 17% | 14% | 19% | 8% | 10% | 8% | 1% | 0% | 1% | 0% | 0% |
| 94 | seq 4 & SP | 0% | 0% | 0% | 0% | 0% | 0% | 0% | 1% | 0% | 1% | 8% | 14% | 14% | 24% | 32% | 8% | 2% | 0% |
| 94 | seq 5 | 0% | 0% | 0% | 0% | 0% | 0% | 0% | 0% | 2% | 2% | 0% | 6% | 15% | 37% | 26% | 11% | 1% | 0% |

Tables 13, 14, 15 and 16 show data collected form various pooling designs.

In order to facilitate quick and accurate analysis of user screening data, we have developed a computer program which identifies the appropriate plate and well position of all potential positive clones. The results will be processed with error correction algorithms to enhance the reliability of the results and compensate for false negative data and false positive data (inherent in many screening technologies like PCR). The results will be displayed as probability scores indicating the likelihood of the resulting plate and well position being correct.

While the invention has been described with reference to more than one preferred embodiment, it is to be clearly understood by those skilled in the art that the invention is not limited thereto to these two embodiments. The general concept of separating the large library set into multiple superpools and then making one, or more than one, set(s) of matrix pools formed by re-pooling a subset of the unique pools into screening pools that will be screened. Each unique pool can be placed in 0, 1 or more than one screening pools, depending on the redundancy of identification required.

What is claimed is:

1. A method for identifying an individual genomic clone DNA insert from a collection of genomic DNA clones comprising the steps of:
   a. arraying the individual genomic DNA clones in 96-well, 384-well, 864-well, or 1536-well microtiter plates comprised of rows and columns with each genomic DNA clone having a specific coordinate locating a well position defined by three or four pools chosen from the group consisting of a plate pool, a row pool, a column pool, and a diagonal pool in a hierarchical structure that is composed of a plate number, a row letter and a column number;
   b. culturing the collection of genomic DNA clones so that a complete set of intermediate subpools is constructed by combining an all individual genomic DNA clone culture in accordance with the hierarchical structure;
   c. isolating an all genomic DNA clone DNA from the all individual genomic DNA clones in the complete set of the intermediate subpools and storing in a stable form;
   d. repooling the complete set of intermediate subpooled genomic DNA clone DNA into a number of Final Screening Pools based on a chosen repooling design, wherein the all individual genomic DNA clone DNA is in at least 4 Final Screening Pools and no more than 8 Final Screening Pools;
   e. screening the number of Final Screening Pools for a DNA sequence of interest, using a screening method selected from the group consisting of Polymerase Chain Reaction (PCR) probing, DNA to DNA hybridization probing, and RNA to DNA probing, to determine the specific coordinate using the chosen repooling design and identify the well position of the DNA sequence of interest.

2. A method for identifying an individual cDNA clone DNA insert from a collection of cDNA clones comprising the steps of:
   a. arraying the individual cDNA clones in 96-well, 384-well, 864-well, or 1536-well microtiter plates comprised of rows and columns with each cDNA clone having a specific coordinate locating a well position defined by three or four pools chosen from the group consisting of a plate pool, a row pool, a column pool, and a diagonal pool in a hierarchical structure that is composed of a plate number, a row letter and a column number;
   b. culturing the collection of cDNA clones so that a complete set of intermediate subpools is constructed by combining an all individual cDNA clone cultures in accordance with the hierarchical structure;
   c. isolating an all cDNA clone DNA from the all individual genomic DNA clones in the complete set of the intermediate subpool and storing in a stable form;
   d. repooling the complete set of intermediate subpooled cDNA clone DNA into a number of Final Screening Pools based on a chosen repooling design, wherein the all individual cDNA clone DNA is in at least 4 Final Screening Pools and no more than 8 Final Screening Pools;
   e. screening the number of Final Screening Pools for a DNA sequence of interest, using a screening method selected from the group consisting of Polymerase Chain Reaction (PCR) probing, DNA to DNA hybridization probing, and RNA to DNA probing, to determine the specific coordinate using the chosen repooling design and identify the well position of the DNA sequence of interest.

3. A method for identifying an individual protein from a collection of expressed proteins or purified proteins comprising the steps of:
   a. arraying the individual proteins in 96-well, 384-well, 864-well, or 1536-well microtiter plates comprised of rows and columns with each protein having a specific coordinate locating a well position defined by three or four pools chosen from the group consisting of a plate pool, a row pool, a column pool, and a diagonal pool in a hierarchical structure that is composed of a plate number, a row letter and a column number;

b. a complete set of intermediate subpools is constructed by combining an all individual proteins in accordance with the hierarchical structure;
c. storing all intermediate subpooled proteins in a stable form;
d. repooling the complete set of intermediate subpooled proteins into a number of final screening pools based on a chosen repooling design, wherein the all individual protein is in at least 4 Final Screening Pools and no more than 8 Final Screening Pools;
e. screening the number of Final Screening Pools for a protein of interest, using a screening method selected from the group consisting of protein to protein probing, antibody to protein probing, DNA to protein probing, RNA to protein probing, and ligand to protein probing, to determine the specific coordinate using the chosen repooling design and identify the well position of the protein sequence of interest.

4. The method of claim 1 wherein the individual genomic DNA clones are selected from the group consisting of BAC clone, fosmid clone, cosmid clone, phage clone, YAC clone, PAC clone, P1 clone and plasmid clone.

* * * * *